US010975018B2

(12) United States Patent
Staghouwer et al.

(10) Patent No.: US 10,975,018 B2
(45) Date of Patent: Apr. 13, 2021

(54) ORGANIC COMPOUNDS

(71) Applicant: GIVAUDAN SA, Vernier (CH)

(72) Inventors: Harm Staghouwer, Eemnes (NL); Chris Thoen, Cincinnati, OH (US); Michel Van Buel, Leusden (NL)

(73) Assignee: Givaudan SA, Vernier (CH)

( * ) Notice: Subject to any disclaimer, the term of this patent is extended or adjusted under 35 U.S.C. 154(b) by 388 days.

(21) Appl. No.: 14/916,830

(22) PCT Filed: Oct. 1, 2014

(86) PCT No.: PCT/EP2014/071021
§ 371 (c)(1),
(2) Date: Mar. 4, 2016

(87) PCT Pub. No.: WO2015/049275
PCT Pub. Date: Apr. 9, 2015

(65) Prior Publication Data
US 2016/0214928 A1    Jul. 28, 2016

(30) Foreign Application Priority Data
Oct. 2, 2013  (GB) ...................................... 1317424

(51) Int. Cl.
C07C 231/24    (2006.01)
A23L 27/00    (2016.01)
A23L 27/20    (2016.01)
A23L 27/21    (2016.01)

(52) U.S. Cl.
CPC .......... C07C 231/24 (2013.01); A23L 27/202 (2016.08); A23L 27/21 (2016.08); A23L 27/88 (2016.08); A23V 2002/00 (2013.01)

(58) Field of Classification Search
CPC ..... C07C 231/24; C07C 231/49; A23L 27/88; A23L 27/21; A23L 27/202; A23V 2002/00
USPC ......................................... 426/534, 536, 650
See application file for complete search history.

(56) References Cited

U.S. PATENT DOCUMENTS

| | | | |
|---|---|---|---|
| 2,835,590 A | 5/1958 | Rusoff et al. | |
| 3,024,272 A | 3/1962 | Hyson et al. | |
| 3,624,114 A | 11/1971 | Morelle | |
| 3,801,633 A | 4/1974 | Toyoshima et al. | |
| 3,878,305 A | 4/1975 | Damico et al. | |
| 3,940,500 A | 2/1976 | Sortwell, III | |
| 3,947,589 A | 3/1976 | Misato et al. | |
| 4,016,287 A | 4/1977 | Eberhardt et al. | |
| 4,066,799 A | 1/1978 | Cornelius et al. | |
| 4,093,740 A | 6/1978 | Fahnenstich et al. | |
| 4,248,859 A | 2/1981 | Roswell et al. | |
| 4,442,090 A | 4/1984 | Kakeya et al. | |
| 4,448,785 A | 5/1984 | Kathawala et al. | |
| 4,479,974 A | 10/1984 | Schenz | |
| 4,757,066 A | 7/1988 | Shiokari et al. | |
| 4,777,195 A | 10/1988 | Hesse et al. | |
| 5,164,414 A | 11/1992 | Vincent et al. | |
| 5,176,934 A | 1/1993 | Lee | |
| 5,286,480 A | 2/1994 | Boggs et al. | |
| 5,312,831 A | 5/1994 | Ayral-Kaloustian et al. | |
| 5,780,090 A | 7/1998 | Frerot et al. | |
| 6,251,931 B1 | 6/2001 | Boger et al. | |
| 7,320,807 B2 | 1/2008 | Asher et al. | |
| 7,981,457 B2 | 7/2011 | Visser et al. | |
| 8,778,437 B2 | 7/2014 | Renes et al. | |
| 8,828,469 B2 | 9/2014 | Langer et al. | |
| 8,945,651 B2 | 2/2015 | Visser et al. | |
| 9,560,846 B2 | 2/2017 | Riera et al. | |
| 9,560,876 B2 | 2/2017 | Riera et al. | |
| 2001/0002257 A1 | 5/2001 | Stolz | |
| 2001/0014695 A1 | 8/2001 | Behl et al. | |
| 2004/0081708 A1 | 4/2004 | Baxter | |
| 2004/0157932 A1 | 8/2004 | Saebo | |
| 2005/0031789 A1 | 2/2005 | Liu et al. | |
| 2007/0282002 A1 | 12/2007 | Maezono et al. | |
| 2008/0038428 A1 | 2/2008 | Visser et al. | |

(Continued)

FOREIGN PATENT DOCUMENTS

| AU | 675778 | 2/1997 |
|---|---|---|
| CN | 101597239 A | 12/2009 |

(Continued)

OTHER PUBLICATIONS

International Search Report for corresponding application PCT/EP2013/070534 dated Aug. 11, 2014.

(Continued)

*Primary Examiner* — Leslie A Wong
(74) *Attorney, Agent, or Firm* — Norris McLaughlin PA

(57) ABSTRACT

A stock solution comprising a compound of formula (I)

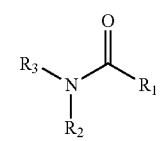

Wherein
$R_1$ together with the carbonyl group to which it is attached is a residue of a carboxylic acid, and $NR_2R_3$, in which $R_3$ is H or together with $R_2$ and the N-atom to which they are attached, a 5-membered ring, is a residue of an amino acid, in particular a proteinogenic amino acid, ornithine, gamma-aminobutyric acid or beta alanine, or a 1-amino cycloalkyl carboxylic acid.

28 Claims, No Drawings

(56) References Cited

U.S. PATENT DOCUMENTS

| | | |
|---|---|---|
| 2008/0038429 A1 | 2/2008 | Visser et al. |
| 2008/0038430 A1 | 2/2008 | Visser et al. |
| 2008/0050500 A1 | 2/2008 | Muranishi et al. |
| 2009/0057618 A1 | 3/2009 | Leinweber et al. |
| 2011/0081473 A1 | 4/2011 | Hamasaki et al. |
| 2013/0022728 A1 | 1/2013 | Popplewell et al. |
| 2015/0044332 A1 | 2/2015 | Shi et al. |
| 2015/0044347 A1 | 2/2015 | Shi et al. |
| 2015/0050408 A1 | 2/2015 | Shi et al. |
| 2015/0064326 A1 | 3/2015 | Shi et al. |
| 2015/0064327 A1 | 3/2015 | Shi et al. |
| 2015/0072060 A1 | 3/2015 | Shi et al. |
| 2015/0086694 A1 | 3/2015 | Shi et al. |

FOREIGN PATENT DOCUMENTS

| | | |
|---|---|---|
| CN | 102028176 A | 4/2011 |
| CN | 102036571 B | 7/2013 |
| DE | 2234399 | 1/1974 |
| EP | 0030448 B1 | 4/1985 |
| EP | 0198348 A2 | 10/1986 |
| EP | 0208279 A1 | 1/1987 |
| EP | 0271816 A2 | 12/1987 |
| EP | 0356784 A2 | 3/1990 |
| EP | 0432039 A2 | 6/1991 |
| EP | 0443891 A1 | 8/1991 |
| EP | 0460566 A2 | 12/1991 |
| EP | 0500332 A2 | 8/1992 |
| EP | 0891674 A1 | 1/1999 |
| EP | 1263286 | 12/2002 |
| EP | 1356744 A1 | 10/2003 |
| EP | 1471052 A1 | 10/2004 |
| EP | 1520850 A2 | 4/2005 |
| EP | 1637042 A1 | 3/2006 |
| EP | 2031092 A2 | 3/2009 |
| EP | 2058297 A1 | 5/2009 |
| EP | 2119373 A1 | 11/2009 |
| EP | 2140770 A1 | 1/2010 |
| EP | 2184051 A1 | 5/2010 |
| EP | 2382871 A1 | 11/2011 |
| EP | 2597082 A1 | 5/2013 |
| FR | 1603799 A | 5/1971 |
| FR | 2765109 A1 | 12/1998 |
| FR | 2878439 A1 | 6/2006 |
| GB | 1130480 | 10/1968 |
| GB | 1426545 | 9/1973 |
| GB | 1377271 | 12/1974 |
| GB | 1436614 | 5/1976 |
| GB | 1560000 | 1/1980 |
| GB | 2200633 A | 8/1988 |
| JP | S4614357 Y1 | 5/1971 |
| JP | S4985244 A | 8/1974 |
| JP | S49124244 | 11/1974 |
| JP | 52-94453 A | 8/1977 |
| JP | S53118516 A | 10/1978 |
| JP | 5690046 A | 7/1981 |
| JP | S56123910 A | 9/1981 |
| JP | S56131365 A | 10/1981 |
| JP | S63156849 A | 6/1988 |
| JP | S63218649 A | 9/1988 |
| JP | H2256608 A | 10/1990 |
| JP | H06157440 A | 6/1994 |
| JP | H08103242 A | 4/1996 |
| JP | H08103242 A1 | 4/1996 |
| JP | H08208453 A | 8/1996 |
| JP | 9313129 A | 12/1997 |
| JP | 2824158 B2 | 11/1998 |
| JP | 2006296356 A | 11/2006 |
| JP | 201229616 A | 2/2012 |
| RU | 2335926 C1 | 10/2008 |
| WO | 8603944 A1 | 7/1986 |
| WO | 8701935 A1 | 4/1987 |
| WO | 9738688 A1 | 10/1997 |
| WO | 0057726 A1 | 10/2000 |
| WO | 01030143 A2 | 5/2001 |
| WO | 0159067 A2 | 8/2001 |
| WO | 02094764 A1 | 11/2002 |
| WO | 0334842 A1 | 5/2003 |
| WO | 2004000787 A2 | 12/2003 |
| WO | 2004075663 A1 | 9/2004 |
| WO | 2005096843 A1 | 10/2005 |
| WO | 2005096844 A1 | 10/2005 |
| WO | 2005102071 A1 | 11/2005 |
| WO | 2006009425 A1 | 1/2006 |
| WO | 2006010590 A1 | 2/2006 |
| WO | 2006046853 A1 | 5/2006 |
| WO | 2008040756 A1 | 4/2008 |
| WO | 2009021558 A1 | 2/2009 |
| WO | 2009141294 A1 | 11/2009 |
| WO | 2010022914 A1 | 3/2010 |
| WO | 2011141685 A2 | 5/2011 |
| WO | 2011105985 A1 | 9/2011 |
| WO | 2011141685 A2 | 11/2011 |
| WO | 2012071293 A2 | 5/2012 |
| WO | 2013010991 A1 | 1/2013 |
| WO | 2013148991 A1 | 10/2013 |
| WO | 2013148997 A1 | 10/2013 |
| WO | 2013149008 A2 | 10/2013 |
| WO | 2013149012 A1 | 10/2013 |
| WO | 2013149019 A1 | 10/2013 |
| WO | 2013149022 A1 | 10/2013 |
| WO | 2013149025 A1 | 10/2013 |
| WO | 2013149031 A2 | 10/2013 |
| WO | 2013149035 A2 | 10/2013 |

OTHER PUBLICATIONS

Written Opinion of the International Searching Authority for corresponding application PCT/EP2013/070534 dated Aug. 11, 2014.
International Search Report for corresponding application PCT/EP2013/070540 dated Nov. 10, 2014.
International Search Report for corresponding application PCT/EP2014/071021 dated Oct. 12, 2014.
Written Opinion of the International Searching Authority for corresponding application PCT/EP2014/071021 dated Oct. 12, 2014.
International Search Report for corresponding application PCT/EP2014/071056 dated Dec. 12, 2014.
International Search Report for corresponding application PCT/US2013/034299 dated Sep. 27, 2013.
Written Opinion of the International Searching Authority for corresponding application PCT/US2013/034299 dated Sep. 27, 2013.
International Search Report for corresponding application PCT/US2013/034335 dated Jul. 12, 2013.
Written Opinion of the International Searching Authority for corresponding application PCT/US2013/034335 dated Jul. 12, 2013.
International Search Report for corresponding application PCT/US2013/034375 dated Jul. 15, 2013.
Written Opinion of the International Searching Authority for corresponding application PCT/US2013/034375 dated Jul. 15, 2013.
International Preliminary Report on Patentability for corresponding application PCT/US2013/034375 dated Oct. 1, 2014.
International Search Report for corresponding application PCT/US2013/034388 dated Jul. 19, 2013.
Written Opinion of the International Searching Authority for corresponding application PCT/US2013/034388 dated Jul. 19, 2013.
International Preliminary Report on Patentability for corresponding application PCT/US2013/034388 dated Oct. 1, 2014.
International Search Report for corresponding application PCT/US2013/062966 dated Sep. 17, 2014.
International Search Report for corresponding application PCT/US2013/062993 dated Jun. 5, 2014.
International Search Report for corresponding application PCT/US2013/063008 dated Aug. 19, 2014.
International Search Report for corresponding application PCT/US2013/063014 dated Aug. 6, 2014.
International Search Report for corresponding application PCT/US2013/034355 dated Oct. 7, 2013.
Written Opinion of the International Searching Authority for corresponding application PCT/US2013/034355 dated Oct. 7, 2013.

(56) References Cited

OTHER PUBLICATIONS

International Preliminary Report on Patentability for corresponding application PCT/US2013/034355 dated Oct. 1, 2014.
Written Opinion of the International Searching Authority for corresponding application PCT/US2013/034363 dated Jul. 18, 2013.
International Preliminary Report on Patentability for corresponding application PCT/US2013/034363 dated Oct. 1, 2014.
International Search Report for corresponding application PCT/US2013/034363 dated Jul. 18, 2013.
International Search Report for corresponding application PCT/US2013/034378 dated Jul. 12, 2013.
Written Opinion of the International Searching Authority for corresponding application PCT/US2013/034378 dated Jul. 12, 2013.
International Preliminary Report on Patentability for corresponding application PCT/US2013/034378 dated Oct. 1, 2014.
International Search Report for corresponding application PCT/US2013/034395 dated Nov. 18, 2013.
Written Opinion of the International Searching Authority for corresponding application PCT/US2013/034395 dated Nov. 18, 2013.
International Preliminary Report on Patentability for corresponding application PCT/US2013/034395 dated Oct. 1, 2014.
International Search Report for corresponding application PCT/US2013/034403 dated Nov. 6, 2013.
Written Opinion of the International Searching Authority for corresponding application PCT/US2013/034403 dated Nov. 6, 2013.
International Preliminary Report on Patentability for corresponding application PCT/US2013/034403 dated Oct. 1, 2014.
T. Amagata, et al. "Gymnastatins F-H, Cytostatic Metabolites from the Sponge-Derived Fungus *Gymnascella dankaliensis*", American Chemical Society and American Society of Pharmacognosy, vol. 69, pp. 1384-1388, 2006.
"Aromat", Wikipedia, the free encyclopedia, http://en.wikipedia.org/wiki/Aromat.
S. H. Burstein, et al., "Potential anti-inflammatory actions of the elmiric (lipoamino) acids", Bioorganic & Medicinal Chemistry, vol. 15, pp. 3345-3355, 2007.
G.M. Dumowchik, et al., "The In vitro effects of Three Lysosomotropic Detergents Against Three Human Tumor Cell Lines", Bioorganic & Medicinal Chemisty Letters, vol. 5, No. 8, pp. 893-898, 1995, Great Britain.
M. Fieser, et al., "Synthetic Emulsify Agents", Chemical Laboratory of Harvord University, pp. 2825-2832, Jun. 20, 1956.
S. N. Georgiades, et al., "Synthetic libraries of tyrosine-derived bacterial metabolites", Bioorganic & Medicinal Chemisty Letters, vol. 18, pp. 3117-3121, 2008.
N. Gregersen, et al., "Gas Chromatographic Mass Spectrometric Identification of N-Dicarboxylmonoglycines", Biomedical Mass Spectrometry, vol. 5, No. 1, pp. 80-83, 1978.
L. Guan, et al., "Synthesis and Anticonvulsant Activity of N-(2-Hydroxy-ethyl)amide Derivatives", Arch. Pharm. Chem. Life Sci. vol. 342, pp. 24-40, 2009.
V. Gududuru, et al., "Synthesis and biological evaluation of novel cytotoxic phospholipids for prostate cancer", Bioorganic & Medicinal Chemisty Letters, vol. 14, pp. 4919-4923, 2004.
C. Leschke, et al., "Alkyl-Substituted Amino Acid Amides and Analogous Di- and Triamines: New Non-Peptide G Protein Activators", Journal of Medicinal Chemistry, vol. 40, pp. 3130-3139, 1997.
A. Leydet, et al., "Polyanion Inhibitors of Human Immunodeficiency Virus and other Viruses, Part 2. Polymerized Anionic Surfactants Derived from Amino Acids and Dipeptides", Journal of Medicinal Chemistry, vol. 39, No. 8, pp. 1626-1634, 1996.
R. H. Mazur, et al., "Structure-Taste Relationships of Aspartic Acid Amides", Journal of Medicinal Chemistry, vol. 13, No. 6, pp. 1217-1221, 1970.
R. C. McKellar, et al., "Antimicrobial activity of fatty N-acylamino acids against Gram-positive foodborne pathogens", Food Microbiology, vol. 9, pp. 67-76, 1992.
C. Menozzi-Smarrito, et al., "Synthesis and Evaluation of New Alkylamides Derived from a-Hydroxysanshool, the Pungent Molecule in Szechuan Pepper", Journal of Agricultural and Food Chemistry, vol. 57, pp. 1982-1989, 2009.
A. Pal, et al., "Molecular mechanism of physical gelation of hydrocarbons by fatty acid amides of natural amino acids", Tetrahedron, vol. 63, pp. 7334-7348, 2007.
Hession, "N-Acetylglutamate and N-Acetylaspartate in Soybeans (*Glycine max* L), Maize (*Zea maize* L.), and Other Foodstuffs", Journal of Agricultural and Food Chemistry, 2008, 56, pp. 9121-9126.
Cameron, "13 Foods with Natural Umami", Readers Digest, (first posted on internet Aug. 3, 2010; downloaded May 28, 2016,from the site: http://www.rd.com/food/recipes-cooking/13-foods-with-natural-umami/) at pp. 1-5.
Doving, et al, "Chemical Senses and Flavour", D. Reidel Publishing Company, vol. 1, No. 4, Oct. 1975, pp. 387-401, USA.
Stenner, "Umami—The Science, Ingredients, and Cooking with the 'Fifth-taste'", published Dec. 11, 2009, downloaded from site: http://www.tulsafood.com/uncategorized/umami-the-science-ingredients-cooking-with-the-fifth-taste, 9 pages.
Kazda, "Sliced Cucumber and Tomato Salad from Life's Ambrosia", copyright 2009, downloaded May 28, 2016 from site: http://www.lifesambrosia.com/print-recipe/?pid=2064 .
Umami Information Center/Umami Rich Foods, downloaded May 28, 2016; screen shot from Wayback Machine, dated May 5, 2011; from the site: http://www.umamiinfo.com/2011/03/umami-rich-food-vegetables.php ; 3 pages.
Roudot-Algaron, "Flavor Constituents of Aqueous Fraction Extracted from Comte Chees by Liquid Carbon Dioxide", Journal of Food Science, vol. 58, No. 5, 1993, pp. 1005-1009.
Umami Information center Web Page/Overview, first posted on the internet on Apr. 30, 2011, as found on the Internet ArchivelWayback Machine at http://www.web.archive.org/web/2011 0430102741/ http://www.umamiinfo.com/umami-rich-food/.
J. P. Ley, "Masking Bitter Taste by Molecules", Chemical Perception, 2008, vol. 1, pp. 58-77.
C. Ma, et al., "Effect of Fatty N-Acylamino Acids on Some Functional Properties of Two Food Proteins", J. AgrigFood. Chem, 1993, vol. 41, pp. 1182-1188.
A. Paquet, "Preparation of some long-chain N-acyl derivatives of essential amino acids for nutritional studies", Canada Journal Biochem., vol. 58, National Research Council of Canada, pp. 573-576, 1980.
M. Gerova, et al., "Self-assembly properties of some chiral N-Palmitoyl amino acid surfactants in aqueous solution", ScienceDirect, Journal of Colloid and Interface Science, 2008, vol. 319, pp. 526-533.
R. Damico, "An Investigation of N-Substituted Methionine Derivatives for Food Supplementation", J. Agr. Food Chem., vol. 23, No. 1, pp. 30-33, 1975.
English translation of first Japanese Office Action for corresponding application JP 2015-503564 dated Dec. 15, 2016.
Written Opinion of the Intellectual Property Office of Singapore for corresponding application CN 11201405104P dated May 30, 2016.
English translation of second Chinese Office Action for corresponding application CN 201380017898.7 dated May 3, 2016.
English translation of first Japanese Office Action for corresponding application JP 2015-503572 dated Dec. 15, 2016.
English translation of second Chinese Office Action for corresponding application CN 201380017847.4 dated May 5, 2016.
English translation of third Chinese Office Action for corresponding application CN 201380017847.4 dated Nov. 22, 2016.
English translation of first Japanese Office Action for corresponding application JP 2015-503573 dated Dec. 14, 2016.
English translation of second Chinese Office Action for corresponding application CN 201380017924.6 dated May 31, 2016.
English translation of first Japanese Office Action for corresponding application JP 2015-503577 dated Jan. 4, 2017.
English translation of first Japanese Office Action for corresponding application JP 2015-503584 dated Jan. 27, 2017.
English translation of first Japanese Office Action for corresponding application JP 2015-503579 dated Oct. 14, 2016.
English translation of second Chinese Office Action for corresponding application CN 201380017825.8 dated May 31, 2016.
English translation of second Chinese Office Action for corresponding application CN 201380017814.x dated Apr. 1, 2016.

(56) References Cited

OTHER PUBLICATIONS

English translation of second Chinese Office Action for corresponding application CN 201380017832.8 dated Mar. 31, 2016.
English translation of second Chinese Office Action for corresponding application CN 201380017831.3 dated Mar. 2, 2016.
Written Opinion of the Intellectual Property Office of Singapore for corresponding application CN 11201405188X dated Sep. 13, 2016.
Written Opinion of the Intellectual Property Office of Singapore for corresponding application CN 11201405295W dated Apr. 15, 2016.
Written Opinion of the Intellectual Property Office of Singapore for corresponding application CN 11201405409P dated May 11, 2016.
Written Opinion of the Intellectual Property Office of Singapore for corresponding application CN 11201405340X dated Mar. 24, 2016.
Written Opinion of the Intellectual Property Office of Singapore for corresponding application CN 11201405342T dated Mar. 23, 2016.
Written Opinion of the Intellectual Property Office of Singapore for corresponding application CN 11201601652X dated Sep. 22, 2016.
Second International Search Report for corresponding application PCT/US2013/034355 dated Oct. 7, 2013.
Second International Search Report for corresponding application PCT/US2013/034299 dated Sep. 27, 2013.
Second International Search Report for corresponding application PCT/US2013/034342 dated Jul. 12, 2013.
International Preliminary Report on Patentability for corresponding application PCT/US2013/034342 dated Oct. 1, 2014.
Written Opinion of the International Searching Authority for corresponding application PCT/US2013/034342 dated Jul. 12, 2013.
Second International Search Report for corresponding application PCT/US2013/034395 dated Nov. 18, 2013.
Second International Search Report for corresponding application PCT/US2013/034403 dated Nov. 6, 2013.
B. Tan, et al., "Identification of endogenous acyl amino acids based on a targeted lipidomics approach", Journal of Lipid Research, vol. 51, pp. 112-119, 2010.
Written Opinion of the Intellectual Property Office of Singapore for corresponding application CN 11201405413S dated Jun. 24, 2016.
U.S. Appl. No. 14/386,048, filed Sep. 18, 2014.
U.S. Appl. No. 14/386,061, filed Sep. 18, 2014.
U.S. Appl. No. 14/386,084, filed Sep. 18, 2014.
U.S. Appl. No. 14/386,090, filed Sep. 18, 2014.
U.S. Appl. No. 14/386,100, filed Sep. 18, 2014.
U.S. Appl. No. 14/386,112, filed Sep. 18, 2014.
U.S. Appl. No. 14/386,126, filed Sep. 18, 2014.
U.S. Appl. No. 14/916,815, filed Mar. 4, 2016.
U.S. Appl. No. 14/916,806, filed Mar. 4, 2016.
U.S. Appl. No. 14/916,765, filed Mar. 4, 2016.
U.S. Appl. No. 14/916,793, filed Mar. 4, 2016.
U.S. Appl. No. 14/916,782, filed Mar. 4, 2016.
U.S. Appl. No. 14/916,830, filed Mar. 4, 2016.
U.S. Appl. No. 14/916,846, filed Mar. 4, 2016.
U.S. Appl. No. 14/916,861, filed Mar. 4, 2016.
U.S. Appl. No. 14/870,598, filed Sep. 30, 2015.
E. Piera, et al., "Qualitative and Quantitative analysis of new alkyl arginine surfactants by high-performance liquid chromatoghraphy and capillary electrophoresis", Journal of Chromatography A, vol. 852, pp. 499-506, 1999.
S. Y. Mhaskar, et al., "Synthesis of N-Acyl Amino Acids and Correlation of Structure with Surfactant Properties of Their Sodium Salts", JAOCS, vol. 67, No. 12, pp. 1015-1019, 1990.
C. L. Penney, et al., "Further studies on the adjuvanticity of stearyl tyrosine and amide analogues", Vaccine, vol. 12, No. 7, pp. 629-632, 1994.
C. W. Phoon, et al., "Isolation and total synthesis of gymnastatin N, a POLO-like kinase 1 active constituent from the fungus *Arachniotus punctatus*", Tetrahedron, vol. 60, pp. 11619-11628, 2004.
C. M. Ranger, et al.,"Mass spectral characterization of fatty acid amides from alfalfa trichomes and their deterrence against the potato leafhopper", Phytochemistry, vol. 66, pp. 529-541, 2005.
M. Schlitzer, et al., "Design, Synthesis and Early Structure-Activity Relationship of Farnesyltransferase Inhibitors Which Mimic Both the Peptidic and the Prenylic Substrate", Bioorganic & Medicinal Chemisty , vol. 8, pp. 1991-2006, 2000.
S. Tadashi, et al., "Aliphatic Acylamino Acids", Pharm. Society Japan, vol. 86, No. 10, pp. 967-972, 1966, Japan.
K. Takao, et al., "Studies on Inhibition of Enzymatic Arginyltransfer Reaction", Chem. Pharm. Bull. vol. 46, No. 7, pp. 1169-1172, 1998, Japan.
C. Toniolo, et al., "Effect of Na-acyl Chain Length on the Membrane-Modifying Properties of Synthetic Analogs of the Lipopeptaibol Trichogin GA IV", Journal of American Chemical Society, vol. 118, pp. 4952-4958, 1996.
K. Watanabe, et al., "Pharmacological Effects in Mice of Anandamide and Its Related Fatty Acid Ethanolamides, and Enhancement of Cataleptogenic Effect of Anandamide by Phenylmethylsulfonyl Fluoride", Bio. Pharm. Bull., vol. 22, No. 4, pp. 366-370, 1999.
A. Kolokouris, et al., "Studies on Pyrrolidinones, Synthesis of some N-Fatty Acylpyroglutamic Acids", J. Heterocyclic Chem., vol. 32, pp. 1489-1492, 1995.
M. Saito, et al., "Sythesis and Inhibitory Activity of Acyl-Peptidyl-Pyrrolidine Derivatives Toward Post-Proline Cleaving Enzyme; A Study of Subsite Specificity", Journal of Enzyme Inhibition, vol. 5, pp. 51-75, 1991, United Kingdom.
Tortoriello, "Targeted Lipidomics in *Drosophila melanogaster* Identifies Novel 2-Monoacylglycerols and N-acyl Amides", vol. 8, Issue 000.7, pp. 1-10, Jul. 2013, www.plosone.org.
Rigo, et al., "Studies on Pyrrolidinones. Synthesis of some N-Fatty Acylpyroglutamic Acids", J. Heterocyclic Chem., vol. 32, pp. 1489-1491, 1995, XP-002224102.
XP-002699514, WPI/Thomson database English abstract of JPH08103242.

ORGANIC COMPOUNDS

This is an application filed under 35 USC 371 of PCT/EP2014/071021 filed 1 Oct. 2014, which in turn claims the priority benefit of GB 1317424.8 filed on 2 Oct. 2013. This application claims the full priority benefit of the foregoing applications, and herein incorporates by reference the entirety of the foregoing documents as if fully set forth herein.

The present invention relates the preparation, purification and isolation of acylamino acids and derivatives thereof. The invention also relates to stock solutions containing said acylamino acids or derivatives, which can be easily formulated into all manner of edible products, such as beverages and foodstuffs.

Acylamino acids and derivatives thereof according to the general formula (I), defined hereinbelow, represent a class of taste-modifying ingredients that can be employed in a wide variety of foodstuffs, beverages and other consumable products.

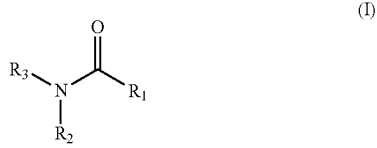

(I)

The compounds may be prepared by the reaction of a fatty acid or a derivative thereof, such as a fatty acid halide or anhydride, with an amino acid, or a derivative thereof. Whereas the synthesis of these compounds appears quite straightforward, applicant found that the compounds are very difficult to purify and isolate from a reaction mixture.

The compounds are valued for their taste modifying properties, as well as the mouth feel or body they impart to flavour compositions or edible products into which they are incorporated. As such, it would be desirable if they could be easily and efficiently separated from any starting materials, side products or solvents of a reaction mixture, which might negatively affect their taste profile. Unfortunately, the compounds do not crystallize readily. Instead, they form an intractable solid mass, which presents a significant technical and commercial obstacle in the path leading towards industrialization of these useful compounds.

There remains a need to provide a method of preparing and purifying these compounds, which can be easily and efficiently carried out on an industrialized scale, and which presents the compounds in a physical form that facilitates their subsequent incorporation into a variety of flavour compositions and edible products, such as beverages and food stuffs.

The invention provides in a first aspect a method of isolating and recovering a compound according to the formula (I) from a reaction mixture comprising said compound in a reaction solvent, characterized in that, prior to removal of the reaction solvent by evaporation, an extraction solvent for the compound, having a higher boiling point than the reaction solvent, is added to the reaction mixture, and wherein after separation of the compound from the reaction solvent, the compound of formula (I) is recovered in the form of a stock solution in said extraction solvent.

Despite the numerous possible solvents that could be employed in the isolation and purification of organic compounds from complex reaction mixtures, the selection of a suitable extraction solvent to form a stock solution of compounds of formula (I) was not a trivial matter. The compounds of formula (I) possess polar groups but also a large hydrophobic chains; as such, there was no systematic relationship between solvent polarity and the ability to dissolve the compounds to form appropriately concentrated solutions. Still further, any solvent with the requisite solvating properties, has to be sufficiently higher boiling than a reaction solvent in order to make separation of the compound from the reaction solvent possible without concomitant evaporative loss of the extraction solvent. Still further, the solvent, in the levels employed in the stock solution, should not present any negative aesthetics when employed in flavour compositions. And finally, it should not hinder further processing of the stock solution into other physical forms. For example, should it be desirable to further process a compound of formula (I) in stock solution, into a powder form, the stock solution solvent should permit the association of the stock solution with various constituents used in the formation of dry powders, such as bulking agents, surfactants, water and the like, in order to facilitate the powder-forming process, and the presence of the solvent should not have a deleterious effect on the physical properties of the powder so formed.

In a particular embodiment of the present invention, the extraction solvent is an organic solvent that is able to produce an at least 0.1%, more particularly an up to 5%, more particularly an up to 10%, still more particular an up to 15%, still more particularly an up to 20%, still more particularly an up to 25%, still more particularly an up to 30% stock solution of a compound of formula (I). The skilled person will appreciate that a stock solution in a range of concentrations between 0.1% to about 30% falls within the purview of the present invention. The present invention also contemplates any range between these values.

In a particular embodiment of the present invention, the extraction solvent may be selected from a water-miscible organic solvent selected from the group consisting of water-miscible alcohols, such as ethanol, glycerol, ethylene glycol, propylene glycol, or derivatives thereof, such as triacetine; or miglyol.

In a particularly preferred embodiment of the present invention the extraction solvent is propylene glycol.

Propylene glycol, is practically tasteless and so is acceptable for use in flavour applications. However, it was somewhat surprisingly able to dissolve sufficient quantities of the compounds of formula (I) in order to make appropriately concentrated stock solutions of the compounds that could be conveniently incorporated into flavour bases.

The invention provides in another of its aspects a method of forming a stock solution comprising the steps of isolating and recovering a compound according to the formula (I) from a reaction mixture comprising said compound in a reaction solvent, characterized in that, prior to removal of the reaction solvent by evaporation, an extraction solvent for the compound, having a higher boiling point than the reaction solvent, is added to the reaction mixture, and wherein after separation of the compound from the reaction solvent, the compound of formula (I) is recovered in the form of a stock solution in said extraction solvent.

In isolating a compound of formula (I) in the extraction solvent, it might be necessary or desirable to further purify the solution of compound of formula (I) in the extraction solvent. This can be achieved by adding to said solution, a non-polar solvent into which contaminants present in the solution can partition. Typical of non-polar solvents include heptane, hexane, pentane, cyclohexane, or aromatics such as toluene or benzene. Accordingly, it is desirable if the extraction solvent for the compounds of formula (I), either alone or with the addition of a small amount of water, e.g. about 5% water, are immiscible with, and will form a two-phase system with, said non-polar solvents. Of the extraction solvents referred to herein, propylene glycol is a particularly useful in this respect.

The invention provides in another of its aspects a stock solution of a compound of formula (I) in a solvent selected from the group consisting of water-miscible alcohols, such as ethanol, glycerol, ethylene glycol, propylene glycol, or derivatives thereof, such as triacetine; or miglyol.

In a particular embodiment of the present invention there is provided a stock solution of a compound of formula (I) in propylene glycol.

In a particular embodiment of the present invention there is provided an at least 5%, more particularly an at least 10%, still more particularly an at least 15%, more particularly still an at least 25% stock solution of a compound of formula (I).

Still more particularly, in an embodiment of the invention there is provided an at least 5%, more particularly an at least 10%, still more particularly an at least 15% stock solution of a compound of formula (I) in propylene glycol.

In yet another aspect of the invention there is provided a stock solution as herein described formed according to a method as herein described.

The stock solution may contain other adjuvants. In a particular embodiment, the stock solution contains an anti-oxidant selected from the group consisting of vitamin C, vitamin E, rosemary extract, antrancine, butylated hydroxyanisole (BHA) and butylated hydroxytoluene (BHT). Anti-oxidants are preferably employed to prevent, or significantly reduce, generation of volatile off notes as a result of degradation of the compounds of formula (I). Anti-oxidants are particularly preferred when the compounds of formula (I) bear a residue of an unsaturated fatty acid. Anti-oxidants are particularly preferred if the fatty acid residue contains more than 1 double bond. Determination of an effective amount of anti-oxidant is within the purview of the skilled person, however amounts in the range of about 10 ppm to 1000 ppm based on the weight of the stock solution may be present.

The compounds of formula (I) are amides. Synthetic procedures for forming amides are well known in the art. The compounds may be formed by the reaction of an amino acid with a carboxylic acid derivative such as a halide, e.g. a chloride or an anhydride in the presence of a base, such as sodium hydroxide. Yield and reaction times may be improved by applying heat to the reaction mixture.

Selection of the reaction solvent system in which to carry out the reaction may be based on solubility considerations, both of the starting materials and the compounds of formula (I). Consideration may also be given to reaction solvent that will promote amide formation. A suitable reaction solvent system is water and a water-miscible organic solvent, or an organic solvent that has some solubility in water. Suitable organic solvents include, therefore, polar ethers such as tetrahydrofuran (THF), 2-methyl-tetrahydrofuran (MeTHF), dimethoxyethane (DME), dimethylisosorbide (DMIS), or mixtures of these ethers.

It is particularly preferred if the water-miscible organic solvent in which the reaction is carried out will phase-separate if a salt is added to the reaction mixture once the reaction has reached completion. In this way, the aqueous saline phase and any aqueous-soluble impurities or unreacted starting materials can be separated and discarded or recycled as appropriate.

In a particular embodiment of the present invention, a method of forming a compound of formula (I) proceeds according to the following procedure:

A fatty acid derivative, such as an acid chloride or acid anhydride, is added to a solution of amino acid in a water/water-miscible organic solvent, in the presence of a base. After stirring for 1 to 2 hours, the reaction mixture is acidified and a two-phase mixture is formed. The phases are separated and the aqueous phase is washed with an organic solvent. The organic solvent washings are combined with the water-miscible organic solvent and the combined solvent solution is washed with brine before being concentrated by evaporation. An extraction solvent having a boiling point higher than the concentrated solvents is added and the lower boiling solvents are removed by evaporation. Optionally, water is added to the extraction solvent and the water/solvent mixture is extracted with a non-polar solvent, such as heptane, in order to remove any unreacted fatty acid derivatives. Thereafter, the extraction solvent may be concentrated to form a stock solution of the present invention.

The compounds of formula (I) are represented by the general formula

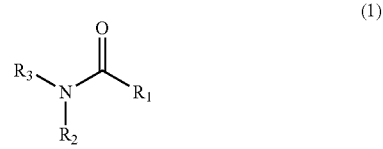

wherein
$R_1$ together with the carbonyl group to which it is attached is a residue of a carboxylic acid, more particular a saturated or unsaturated fatty acid, and $NR_2R_3$, in which $R_3$ is H or together with $R_2$ and the N-atom to which they are attached, a 5-membered ring, is a residue of an amino acid, in particular a proteinogenic amino acid, ornithine, gamma-aminobutyric acid or beta alanine, or a 1-amino cycloalkyl carboxylic acid.

The compounds of formula (I) may also be presented in the form of their edible salts. Edible salts include those typically employed in the food and beverage industry and include chlorides, sulphates, phosphates, gluconates, sodium, citrates, carbonates, acetates and lactates. All of the compounds of formula (I) described hereinabove and hereinbelow, may also be in the form their esters, that is, the carboxylic acid functionality of the amino acid moiety, may be esterified.

The proteinogenic amino acids are alanine (Ala), cysteine (Cys), aspartic acid (Asp), phenylalanine (Phe), glutamic acid (Glu), histidine (His), isoleucine (Ile), lysine (Lys), leucine (Leu), methionine (Met), asparagines (Asn), glutamine (Gln), arginine (Arg), serine (Ser), threonine (Thr), valine (Val), tryptophan (Trp), tyrosine (Tyr), proline (Pro) or glycine (Gly).

The three letter codes in parentheses are common abbreviations used in relation to the amino acids and they shall be used henceforth.

The carboxylic acids can likewise be represented by abbreviations. Henceforth, the carboxylic acid residues may be referred to by the abbreviation Cn, wherein "n" represents the number of carbon atoms in the residue. For example, the residue of an 18 carbon acid may be abbreviated as C18. Still further, if the 18 carbon acid is saturated, e.g. stearic acid. It may be abbreviated as C18:0 (because it contains zero double bonds), whereas an 18 carbon acid having one double bond—e.g. oleic acid—may be abbreviated as C18:1. Still further, if the C18 acid has a single double bond in the cis configuration, then it can be abbreviated as C18:1c. Similarly, if the double bond was in the trans configuration, then the abbreviation becomes C18:1t.

The compounds of formula (I) can also be represented in terms of these abbreviations. For example, the compound of formula (I) consisting of a residue of a C18 carboxylic acid and a residue of the amino acid Proline can be represented by the abbreviation C18-Pro. For simplicity the compounds of formula (I) henceforth may be represented in this abbreviated form.

As is evident from the above formula (I), an amino nitrogen atom on the amino acid residue is bound to a carbonyl carbon atom of the carboxylic acid residue to form an amide linkage. Some amino acids (ornithine and Lysine) have more than one amine groups, and the amide linkage can be formed at any of these amino groups.

In a particular embodiment of the present invention the carboxylic acid residue is a residue of a fatty acid.

The fatty acid residue may be the residue of a C8 to C22 fatty acid, which may be saturated or unsaturated. The fatty acid may be mammalian or non-mammalian. A mammalian fatty acid is a natural or synthetic fatty acid that is identical in structure to one naturally produced in a mammal, including, but not limited to, myristic acid, palmitic acid, stearic acid, oleic acid, linoleic acid, linolenic acid, eicosatrienoic acid, arachidonic acid, eicosapentenoic acid, and docosatetraenoic acid. A non-mammalian fatty acid is a natural or synthetic fatty acid not normally produced by a mammal, including, but not limited to, pentadecanoic acid; heptadecanoic acid; nonadecanoic acid; heneicosanoic acid; 9-trans-tetradecenoic acid; 10-trans-pentadecenoic acid; 9-trans-hexadecenoic acid; 10-trans-heptadecenoic acid; 10-trans-heptadecenoic acid; 7-trans-nonadecenoic acid; 10,13-nonadecadienoic acid; 11-trans-eicosenoic acid; and 12-transhenicosenoic acid.

The fatty acid residues may be saturated or unsaturated. If they are unsaturated, it is preferred that they have 1, 2 or 3 double bonds, which may in cis- or trans-configuration. More particularly, the preferred fatty acid residues are C16 to C18, and may be saturated or unsaturated.

The skilled person will appreciate, however, that natural sources of these fatty acids, for example almond oil, avocado oil, castor oil, coconut oil, corn oil, cottonseed oil, olive oil, peanut oil, rice bran oil, safflower oil, sesame oil, soybean oil, sunflower oil, palm oil and canola oil, each consist of a complex mixture of fatty acids. For example, safflower oil is predominately a source of the C18:2 linoleic acid, nevertheless it may contain other fatty acids, such as linolenic acid (C18:3) and palmitic acid (C16:0), amongst others. Accordingly, reference herein to a compound containing a particular fatty acid residue, for example a residue of C18 fatty acid, may be a reference to a pure, or substantially pure C18 fatty acid residue, or it may relate to a mixture of fatty acid residues with the predominant residue being a C18 residue.

The presentation of compounds of formula (I) in the form of stock solutions is particularly preferred for those compounds having a relatively long fatty acid chain, for example those compounds formed from C16 to C22 fatty acids, more particularly C16 to C18 fatty acids. Stock solutions are also particularly preferred for compounds formed from fatty acids of natural origin, i.e. fatty acids contained in natural oils that exist in the form of mixtures of fatty acids, rather than the fatty acids in pure form. Stock solutions are also preferred for fatty acids that are unsaturated.

Compounds of formula (I) may contain chiral atoms, and as such they may exist in racemic form, as a mixture of stereoisomers or as resolved as single isomers. The use of the term "a compound of formula (I)" may refer to both mixtures of isomers or resolved single isomers.

In particular, the compounds of formula (I) may contain the residue of D- or L-amino acids.

In an embodiment of the the present invention the compounds of formula (I) are represented by the formula

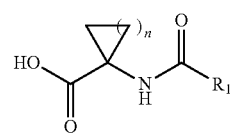

wherein
$R_1$, is hereinabove defined, and
n is 1, 2, 3 or 4.

The preferred compounds are those wherein "n" is 1.

The amino acid residue disclosed in the above formula may be abbreviated as "ACCA".

The compounds include C8-ACCA, C9-ACCA, C10-ACCA, C12-ACCA, C14-ACCA, C16-ACCA, C18-ACCA, C20-ACCA and C22-ACCA.

The compounds include C8-ACCA, C9-ACCA, C10-ACCA, C12-ACCA, C14-ACCA, C16-ACCA, C18-ACCA, C20-ACCA and C22-ACCA, wherein the carboxylic acid residue is saturated.

The compounds include C8-ACCA, C9-ACCA, C10-ACCA, C12-ACCA, C14-ACCA, C16-ACCA, C18-ACCA, C20-ACCA and C22-ACCA, wherein the carboxylic acid residue is unsaturated and contains 1, 2 or 3 double bonds. The double bonds may be in cis-configuration, trans-configuration or a mixture of cis- and trans-configuration.

The compounds include those specified above wherein the cycloalkane ring in the amino acid residue is cyclopropane (n=1).

Particularly preferred compounds are N-palmitoyl 1-amino-cyclopropyl carboxylic acid (C16:0-ACCA), N-stearoyl 1-amino-cyclopropyl carboxylic acid (C18:0-ACCA), N-linoleoyl 1-amino-cyclopropyl carboxylic acid (C18:2-ACCA), N-linolenoyl 1-amino-cyclopropyl carboxylic acid (C18:3-ACCA), N-oleoyl 1-amino-cyclopropyl carboxylic acid (C18:1-ACCA), N-(9-palmitenoyl) 1-amino-cyclopropyl carboxylic acid (C16:1-ACCA), N-decanoyl 1-amino-cyclopropyl carboxylic acid (C10:0-ACCA) and N-geranoyl 1-amino-cyclopropyl carboxylic acid (C10:2-ACCA).

In another embodiment the compounds of formula (I) are represented by the formula

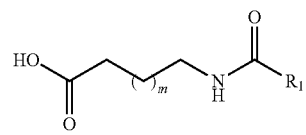

wherein
$R_1$, is hereinabove defined, and
m is 0 or 1.

It will be apparent to the person skilled in the art that when m is 1, the amino acid residue is a residue of gamma amino butyric acid (GABA), whereas when m is 0, the amino acid residue is a residue of beta-alanine (Beta Ala). Both the compounds of formula (I) wherein m is 1 and the amino acid residue is a residue of GABA, and the compounds of formula (I) wherein m is 0 and the amino acid residue is a residue of beta-alanine, their edible salts, as well as their use in edible products, are all embodiments of the present invention.

These compounds are particularly useful to incorporate into an edible product to impart a remarkable mouthfeel, body and enhanced fat perception; or an enhanced umami or salt taste; or a cooling and richness. They are particularly useful in applications low in fat, salt and umami. They are also useful in fat-free formulations such as beverages and oral care applications. They also find use in dairy applications and in vanilla, cocoa and chocolate.

The compounds include C8-GABA, C9-GABA, C10-GABA, C12-GABA, C14-GABA, C16-GABA, C18-GABA, C20-GABA and C22-GABA.

The compounds include C8-GABA, C9-GABA, C10-GABA, C12-GABA, C14-GABA, C16-GABA, C18-GABA, C20-GABA and C22-GABA, wherein the carboxylic acid residue is saturated.

The compounds include C8-GABA, C9-GABA, C10-GABA, C12-GABA, C14-GABA, C16-GABA, C18-GABA, C20-GABA and C22-GABA, wherein the carboxylic acid residue is unsaturated and contains 1, 2 or 3 double bonds. The double bonds may be in cis-configuration, trans-configuration or a mixture of cis- and trans-configuration.

Particularly preferred compounds include C10-GABA, C12-GABA, more particularly C12:1-GABA, C14-GABA, C16-GABA, more particularly C16:1-GABA, C18-GABA, more particularly C18:1-GABA, still more particularly C18:1c-GABA and C18:1t-GABA. Most preferred is a compound C18:2-GABA.

The compounds include C8-Beta Ala, C9-Beta Ala, C10-Beta Ala, C12-Beta Ala, C14-Beta Ala, C16-Beta Ala, C18-Beta Ala, C20-Beta Ala and C22-Beta Ala.

The compounds include C8-Beta Ala, C9-Beta Ala, C10-Beta Ala, C12-Beta Ala, C14-Beta Ala, C16-Beta Ala, C18-Beta Ala, C20-Beta Ala and C22-Beta Ala, wherein the carboxylic acid residue is saturated.

The compounds include C8-Beta Ala, C9-Beta Ala, C10-Beta Ala, C12-Beta Ala, C14-Beta Ala, C16-Beta Ala, C18-Beta Ala, C20-Beta Ala and C22-Beta Ala, wherein the carboxylic acid residue is unsaturated and contains 1, 2 or 3 double bonds. The double bonds may be in cis-configuration, trans-configuration or a mixture of cis- and trans-configuration.

A preferred compound is C18:2-Beta Ala.

In another embodiment the compounds of formula (I) are represented by the formula

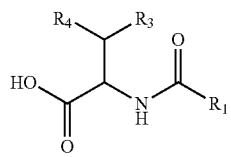

wherein
$R_1$, is hereinabove defined,
$R_3$ is hydrogen or methyl, and
$R_4$ is methyl, ethyl or iso-propyl.

Particular compounds are those in which $R_3$ is hydrogen and $R_4$ is iso-propyl; $R_3$ is methyl and $R_4$ is methyl; and $R_3$ is methyl and $R_4$ is ethyl. The skilled person will appreciate that the amino acid residue in which $R_3$ is hydrogen and $R_4$ is iso-propyl is the residue of Leucine (Leu); whereas the amino acid residue in which $R_3$ is methyl and $R_4$ is methyl is the residue of Valine (Val); and the amino acid residue in which $R_3$ is methyl and $R_4$ is ethyl is the residue of iso-Leucine (Ile).

The compounds in which $R_3$ is hydrogen and $R_4$ is iso-propyl; $R_3$ is methyl and $R_4$ is methyl; and $R_3$ is methyl and $R_4$ is ethyl, as well as their use in edible products, are all embodiments of the present invention.

These compounds are particularly useful to enhance authentic fruit profiles, They may also find use in fruit flavoured milk, yoghurt and ice creams.

The compounds include C8-Leu, C9-Leu, C10-Leu, C12-Leu, C14-Leu, C16-Leu, C18-Leu, C20-Leu and C22-Leu.

The compounds include C8-Leu, C9-Leu, C10-Leu, C12-Leu, C14-Leu, C16-Leu, C18-Leu, C20-Leu and C22-Leu, wherein the carboxylic acid residue is saturated.

The compounds include C8-Leu, C9-Leu, C10-Leu, C12-Leu, C14-Leu, C16-Leu, C18-Leu, C20-Leu and C22-Leu, wherein the carboxylic acid residue is unsaturated and contains 1, 2 or 3 double bonds. The double bonds may be in cis-configuration, trans-configuration or a mixture of cis- and trans-configuration.

Particular compounds bearing the Leu residue include N-palmitenoyl-L-leucine, N-palmitoyl-L-leucine, N-linolenoyl-L-leucine, N-linoleoyl-L-leucine and N-oleoyl-L-leucine.

The compounds include C8-Ile, C9-Ile, C10-Ile, C12-Ile, C14-Ile, C16-Ile, C18-Ile, C20-Ile and C22-Ile.

The compounds include C8-Ile, C9-Ile, C10-Ile, C12-Ile, C14-Ile, C16-Ile, C18-Ile, C20-Ile and C22-Ile, wherein the carboxylic acid residue is saturated.

The compounds include C8-Ile, C9-Ile, C10-Ile, C12-Ile, C14-Ile, C16-Ile, C18-Ile, C20-Ile and C22-Ile, wherein the carboxylic acid residue is unsaturated and contains 1, 2 or 3 double bonds. The double bonds may be in cis-configuration, trans-configuration or a mixture of cis- and trans-configuration.

A particularly preferred compound bearing the Ile residue is N-oleoyl-Ile.

The compounds include C8-Val, C9-Val, C10-Val, C12-Val, C14-Val, C16-Val, C18-Val, C20-Val and C22-Val.

The compounds include C8-Val, C9-Val, C10-Val, C12-Val, C14-Val, C16-Val, C18-Val, C20-Val and C22-Val, wherein the carboxylic acid residue is saturated.

The compounds include C8-Val, C9-Val, C10-Val, C12-Val, C14-Val, C16-Val, C18-Val, C20-Val and C22-Val, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Val residue include N-palmitenoyl-L-valine, N-palmitoyl-L-valine, N-linolenoyl-L-valine, N-linoleoyl-L-valine and N-oleoyl-L-valine.

In another embodiment the compounds of formula (I) are represented by the formula

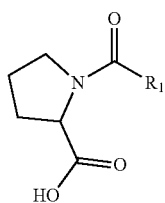

wherein
R$_1$, is hereinabove defined.

The skilled person will appreciate that the amino acid residue in the compounds defined above is the proline residue (Pro).

These compounds are particularly effective to enhance juiciness and typical citrus authenticity. They find use particularly in powdered soft drinks and beverages, and also in dairy applications, such as fruit flavoured milk, yoghurt and ice creams.

The compounds include C8-Pro, C9-Pro, C10-Pro, C12-Pro, C14-Pro, C16-Pro, C18-Pro, C20-Pro and C22-Pro.

The compounds include C8-Pro, C9-Pro, C10-Pro, C12-Pro, C14-Pro, C16-Pro, C18-Pro, C20-Pro and C22-Pro, wherein the carboxylic acid residue is saturated.

The compounds include C8-Pro, C9-Pro, C10-Pro, C12-Pro, C14-Pro, C16-Pro, C18-Pro, C20-Pro and C22-Pro, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Pro residue N-geranoyl-Pro, N-palmitoyl-Pro, N-palmiteneoyl-Pro, N-stearoyl-Pro, N-linoleoyl-Pro and N-linolenoyl-Pro.

In another embodiment of the invention, the compounds of formula (I) are represented by the formula

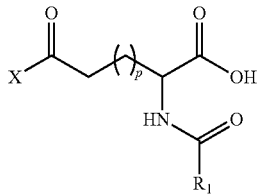

wherein
R$_1$, is hereinabove defined,
X is OH or NH$_2$ and
P is 0 or 1.

The skilled person will appreciate that when p is 0 and X is OH, the amino acid residue set forth in the above formula is a residue of aspartic acid, whereas when p is 1, and X is OH the residue is that of glutamic acid, whereas when p is 0 and X is NH$_2$, the residue is that of asparagine (Asn), and when p is 1 and X is NH$_2$, the residue is that of glutamine (Gln).

The compounds bearing an aspartic acid residue, the compounds bearing a glutamic acid residue, the compounds bearing an asparagine residue, and the compounds bearing a glutamine residue, as well as their edible salts, and their use in edible products, each represent particular embodiments of the present invention.

These compounds are particularly useful to enhance savoury character, mouthfeel and overall flavour performance, juiciness and salivation. They may find use in low salt, low umami and low fat as well as fruit flavour drinks as well as dairy applications.

The compounds include C8-Glu, C9-Glu, C10-Glu, C12-Glu, C14-Glu, C16-Glu, C18-Glu, C20-Glu and C22-Glu.

The compounds include C8-Glu, C9-Glu, C10-Glu, C12-Glu, C14-Glu, C16-Glu, C18-Glu, C20-Glu and C22-Glu, wherein the carboxylic acid residue is saturated.

The compounds include C8-Glu, C9-Glu, C10-Glu, C12-Glu, C14-Glu, C16-Glu, C18-Glu, C20-Glu and C22-Glu, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Glu residue include N-geranoyl-Glu, N-palmitoyl-Glu, N-palmitenoyl-Glu, N-stearoyl-Glu, N-linoleoyl-Glu and N-linolenoyl-Glu.

The compounds include C8-Asp, C9-Asp, C10-Asp, C12-Asp, C14-Asp, C16-Asp, C18-Asp, C20-Asp and C22-Asp.

The compounds include C8-Asp, C9-Asp, C10-Asp, C12-Asp, C14-Asp, C16-Asp, C18-Asp, C20-Asp and C22-Asp, wherein the carboxylic acid residue is saturated.

The compounds include C8-Asp, C9-Asp, C10-Asp, C12-Asp, C14-Asp, C16-Asp, C18-Asp, C20-Asp and C22-Asp, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Asp residue include N-geranoyl-Asp, N-palmitoyl-Asp, N-palmitenoyl-Asp, N-stearoyl-Asp, N-linoleoyl-Asp and N-linolenoyl-Asp.

The compounds include C8-Gln, C9-Gln, C10-Gln, C12-Gln, C14-Gln, C16-Gln, C18-Gln, C20-Gln and C22-Gln.

The compounds include C8-Gln, C9-Gln, C10-Gln, C12-Gln, C14-Gln, C16-Gln, C18-Gln, C20-Gln and C22-Gln, wherein the carboxylic acid residue is saturated.

The compounds include C8-Gln, C9-Gln, C10-Gln, C12-Gln, C14-Gln, C16-Gln, C18-Gln, C20-Gln and C22-Gln, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Gln residue include N-geranoyl-Gln, N-palmitoyl-Gln, N-palmitenoyl-Gln, N-stearoyl-Gln, N-linoleoyl-Gln and N-linolenoyl-Gln.

The compounds include C8-Asn, C9-Asn, C10-Asn, C12-Asn, C14-Asn, C16-Asn, C18-Asn, C20-Asn and C22-Asn.

The compounds include C8-Asn, C9-Asn, C10-Asn, C12-Asn, C14-Asn, C16-Asn, C18-Asn, C20-Asn and C22-Asn, wherein the carboxylic acid residue is saturated.

The compounds C8-Asn, C9-Asn, C10-Asn, C12-Asn, C14-Asn, C16-Asn, C18-Asn, C20-Asn and C22-Asn, wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Asn residue include N-geranoyl-Asn, N-palmitoyl-Asn, N-palmitenoyl-Asn, N-stearoyl-Asn, N-linoleoyl-Asn and N-linolenoyl-Asn.

In another embodiment the compounds of formula (I) are represented by the formula

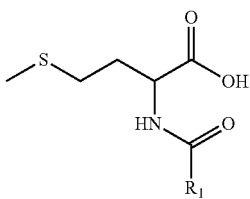

wherein
$R_1$, is hereinabove defined.

The skilled person will appreciate that in the above formula the amino acid residue is the residue of methionine (Met).

These compounds are particularly effective to enhance juiciness and salivation, as well as the authenticity of fruits. They also are useful in soft drinks applications for their masking properties.

The compounds include C8-Met, C9-Met, C10-Met, C12-Met, C14-Met, C16-Met, C18-Met, C20-Met and C22-Met.

The compounds include C8-Met, C9-Met, C10-Met, C12-Met, C14-Met, C16-Met, C18-Met, C20-Met and C22-Met, wherein the carboxylic acid residue is saturated.

The compounds include C8-Met, C9-Met, C10-Met, C12-Met, C14-Met, C16-Met, C18-Met, C20-Met and C22-Met wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Met residue include N-geranoyl-Met, N-palmitoyl-Met, N-palmitenoyl-Met, N-stearoyl-Met, N-linoleoyl-Met and N-linolenoyl-Met.

In another embodiment the compounds of formula (I) are represented by the formula

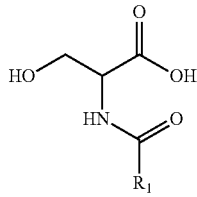

wherein
$R_1$, is hereinabove defined.

The skilled person will appreciate that in the above formula the amino acid residue is the residue of serine (Ser).

These compounds find particular use in low salt, umami and fat, fruit flavoured beverages and/or dairy applications.

The compounds include C8-Ser, C9-Ser, C10-Ser, C12-Ser, C14-Ser, C16-Ser, C18-Ser, C20-Ser and C22-Ser.

The compounds include C8-Ser, C9-Ser, C10-Ser, C12-Ser, C14-Ser, C16-Ser, C18-Ser, C20-Ser and C22-Ser, wherein the carboxylic acid residue is saturated.

The compounds include C8-Ser, C9-Ser, C10-Ser, C12-Ser, C14-Ser, C16-Ser, C18-Ser, C20-Ser and C22-Ser wherein the carboxylic acid residue is unsaturated and contains 1, 2 or 3 double bonds. The double bonds may be in cis-configuration, trans-configuration or a mixture of cis- and trans-configuration.

Particularly preferred compounds bearing the Ser residue include N-palmitoyl-Ser, N-palmitenoyl-Ser, N-stearoyl-Ser, N-linoleoyl-Ser and N-linolenoyl-Ser.

Other compounds useful in the present invention include:
N-octanoyl-L-phenylalanine, N-eicosanoyl-L-phenylalanine, N-palmitoleoyl-L-phenylalanine, N-palmitoyl-L-phenylalanine, N-linolenoyl-L-phenylalanine, N-linoleoyl-L-phenylalanine, N-oleoyl-L-phenylalanine, N-SDA-L-phenylalanine, N-DPA-L-phenylalanine, and N-tetracosahexaenoyl-L-phenylalanine;
N-palmitoyl-L-alanine, N-linolenoyl-L-alanine, N-linoleoyl-L-alanine;
N-palmitoyl-L-tyrosine, N-linoleoyl-L-tyrosine, N-oleoyl-L-tyrosine, N-linolenoyl-L-tyrosine;
N-palmitoyl-L-tryptophan, N-linolenoyl-L-tryptophan, N-linoleoyl-L-tryptophan; and
N-linoleoyl-glycine.

The stock solutions containing compounds of formula (I) can impart organoleptic properties to flavour compositions and edible products to which they are added. In particular, they impart highly intense, authentic and harmonious flavour, and a roundness and fullness to flavour compositions and edible products containing them.

This finding was surprising considering that when the compounds themselves merely exhibit a disappointing, faintly fatty taste profile. As such, they appeared to be quite unsuitable for use in flavour applications. Only their combination with flavour co-ingredients and the judicious selection of their usage levels was it possible to discover the remarkable organoleptic properties of these compounds. Their effect on edible products is quite unusual in that they actually complement, lift or accentuate the essential or authentic flavour and mouth feel characteristics of the foods or beverages in which they are incorporated. Accordingly, the stock solutions containing compounds of formula (I) find utility in a broad spectrum of applications in the food and beverage industry, as well as in health and wellness.

Accordingly, the invention provides in another of its aspects, a method of conferring flavour and/or mouthfeel to, or improving taste and/or mouthfeel of a flavour composition or edible product, which method comprises adding to said composition or product a stock solution containing a compound of formula (I) as defined herein.

The organoleptic effects are observed when the stock solutions containing compounds of formula (I) are incorporated into flavour compositions and edible products containing one or more flavour co-ingredients.

The flavour co-ingredients may be sugars, fats, salt (e.g. sodium chloride), MSG, calcium ions, phosphate ions, organic acids, proteins, purines and mixtures thereof.

In a particular embodiment, sugars are present in amounts of 0.001% to 90%, more particularly 0.001% to 50%, still more particularly 0.001% to 20% based on the total weight of an edible product.

In a particular embodiment, fats are present in amounts of 0.001% to 100%, more particularly 0.001% to 80%, more particularly 0.001% to 30%, still more particularly 0.001% to 5% based on the total weight of an edible product.

In a particular embodiment, salt (e.g. sodium chloride) is present in amounts of 0.001% to 20%, more particularly 0.001% to 5% based on the total weight of an edible product.

In a particular embodiment, MSG is present in amounts of 0.001% to 2% based on the total weight of an edible product.

In a particular embodiment, calcium is present in amounts of 0.001% to 50% more particularly 0.001% to 20%, still more particularly 0.001% to 1% based on the total weight of an edible product.

In a particular embodiment, organic acids are present in amounts of 0.001% to 10%, more particularly 0.001% to 7% based on the total weight of an edible product.

Types of organic acids include citric, malic, tartaric, fumaric, lactic, acetic and succinic. Types of edible products containing organic acids include beverages, such as carbonated soft drink beverages, still beverages, Juices, powdered soft drinks, liquid concentrates, alcoholic beverages and functional beverages.

In a particular embodiment, phosphorus is present in an amount up to 0.5% by weight of an edible product. Typically phosphorus will be present as a phosphate or as phosphoric acid.

In a particular embodiment, purines are present in an amount up to 0.5% by weight of an edible product. The term "purines" include ribonucleotides such as IMP and GMP.

In preparing the flavour compositions of the present invention, the stock solutions may be simply mixed into a flavour composition, or it may be further diluted into other solvents, such as triacetin, miglyol or other solvent useful in food stuffs and beverages.

However, it might be desirable to further process the stock solutions, for example, drying them in a dispersive evaporative process, such as spray drying, fluid bed drying, drum drying, film drying and vacuum drying order to present the compounds of formula (I) into a powdered form.

Accordingly, in another aspect of the present invention, there is provided a powder formulation comprising a compound of formula (I) formed from a stock solution as defined herein.

In a particular embodiment, the powder is formed according to a spray drying process.

Spray dried powders according to the invention may be prepared according to methods and apparatus known in the art for producing powders on an industrial scale. A particularly suitable method is spray drying. Spray drying techniques and apparatus are well known in the art and need no detailed discussion herein. The spray drying techniques, apparatus and methods described in US2005/0031769 and US2013/0022728, as well as those techniques, apparatus and methods described in those documents are suitable for producing powder compositions of the present invention and are herein incorporated by reference in their entirety.

In particular, powder compositions may be prepared by mixing the stock solution with a suitable carrier material and optionally additional flavour co-ingredients, and optionally a surfactant, and spraying the resultant mixture a conventional spray dry apparatus as referred to hereinabove.

The stock solutions of the present invention would not be conventionally considered as the most suitable materials to employ in a drying operation. The solvents employed in forming the stock solutions, and in particular the water-miscible alcohols, can affect the powder quality of a finished dried powder. In particular, the use of such solvents can cause caking of powders. The use of propylene glycol can be particularly problematic in this regard. Nevertheless, applicant found that employing sufficiently concentrated stock solutions, such as about 5 to about 30%, more particularly about 10 to 15% solutions, it was possible to obtain good powder quality.

The applicant also found that selection of the bulking material (or carrier material as it is also referred to) used in the composition to be dried can also improve the quality of the powder quality notwithstanding the use of these solvents in the stock solution.

The carrier material may be chosen from modified starches, such as octenyl succinic anhydride (OSA), starch and maltodextrins; gum Arabic, modified gum Arabic, dextrins, animal and vegetable derived proteins, such as gelatin, soy, pea, whey and milk proteins; low molecular weight sugars, such as glucose, fructose, sucrose, maltose, maltotriose, lactose, and the like; polyols; such as mannitol, xylitol, sorbitol, maltitol, lactitol; and salts of food acids, such as magnesium citrate.

Preferred carrier materials are those having relatively high Tg, A carrier material having a Tg of between 80 and 120 degrees centigrade may be considered high Tg carrier materials. Similarly, a carrier material equilibrated under conditions of ambient temperature and 50% relative humidity, which exhibits a Tg of at least 40 degrees centigrade, may be considered a high Tg carrier material. Tg can be measured using DSC techniques known generally in the art. Suitable equilibration conditions are described in the examples hereinbelow.

Exemplary high Tg carrier materials are the modified starches, proteins and gum Arabic. Particular high Tg carriers include maltodextrins having a dextrose equivalent (DE) of about 3 to 25, more particularly 3 to 20.

Accordingly, in another aspect of the present invention there is provided a dried powder formulation comprising a compound of formula (I), and a carrier material selected from the group comprising any of the high Tg carrier materials referred to hereinabove, more particular a high Tg carrier referred to hereinabove that is a maltodextrin having dextrose equivalent of 3 to 25, more particularly 3 to 20, or gum Arabic.

Dried powders formed from high Tg carrier materials are physically stable, that is, they are not prone to caking.

The compound of formula (I) may be loaded onto a dried powder in any desired amount. However, it is preferred if a compound of formula (I) is loaded in an amount present in a dried powder in an amount of about 0.1 up to about 10% by weight, more particularly about 0.1 to 5% by weight, still more particularly 0.1 to 3% by weight, e.g. 1.5% by weight, based on the total weight of the powder. The loading is determined by the solubility of the compound of formula (I) in the stock solution, as well as the need to keep the concentration of the stock solution solvent as low as possible in the spray drying composition to prevent or reduce the incidence of subsequent issues with powder caking.

The compounds of formula (I), for example, in the form of a stock solution, or in the form of a dried powder, may be incorporated into an edible product, alone, or in the form of a flavour composition comprising one or more flavour co-ingredients.

A flavour composition comprising a stock solution or dried powder containing a compound according to the formula (I) forms a further aspect of the present invention.

In an embodiment of the present invention, the flavour composition comprises a compound of formula (I) and at least one flavour co-ingredient.

In a particular embodiment of the present invention the flavour composition comprises:
 i) a compound according to formula (I);
 ii) at least one flavour co-ingredient;
 iii) optionally a carrier material; and
 iv) optionally at least one adjuvant.

The term "flavour co-ingredient" is an ingredient that is able to contribute or impart or modify in a positive or pleasant way the taste of a flavour composition or an edible product.

All manner of flavour co-ingredients may be employed in a flavour composition or edible product according to the present invention, including, but not limited to natural flavours, artificial flavours, spices, seasonings, and the like. Flavour co-ingredients include synthetic flavour oils and flavouring aromatics and/or oils, oleoresins, essences, distillates, and extracts derived from plants, leaves, flowers, fruits, and so forth, and combinations comprising at least one of the foregoing.

Flavour oils include spearmint oil, cinnamon oil, oil of wintergreen (methyl salicylate), peppermint oil, Japanese mint oil, clove oil, bay oil, *anise* oil, *Eucalyptus* oil, thyme oil, cedar leaf oil, oil of nutmeg, allspice, oil of sage, mace, oil of bitter almonds, and *Cassia* oil; useful flavouring agents include artificial, natural and synthetic fruit flavours such as vanilla, and citrus oils including lemon, orange, lime, grapefruit, yazu, sudachi, and fruit essences including apple, pear, peach, grape, blueberry, strawberry, raspberry, cherry, plum, prune, raisin, *cola, guarana*, neroli, pineapple, apricot, banana, melon, apricot, *ume*, cherry, raspberry, blackberry, tropical fruit, *mango*, mangosteen, pomegranate, *Papaya* and the like.

Additional exemplary flavours imparted by a flavouring agent include a milk flavour, a butter flavour, a cheese flavour, a cream flavour, and a yogurt flavour; a vanilla flavour; tea or coffee flavours, such as a green tea flavour, an oolong tea flavour, a tea flavour, a cocoa flavour, a chocolate flavour, and a coffee flavour; mint flavours, such as a peppermint flavour, a spearmint flavour, and a Japanese mint flavour; spicy flavours, such as an asafetida flavour, an *ajowan* flavour, an *anise* flavour, an *Angelica* flavour, a fennel flavour, an all spice flavour, a cinnamon flavour, a chamomile flavour, a mustard flavour, a *cardamom* flavour, a caraway flavour, a cumin flavour, a clove flavour, a pepper flavour, a coriander flavour, a *sassafras* flavour, a savoury flavour, a *zanthoxyli fructus* flavour, a *perilla* flavour, a *juniper* berry flavour, a ginger flavour, a star *anise* flavour, a horseradish flavour, a thyme flavour, a tarragon flavour, a dill flavour, a *capsicum* flavour, a nutmeg flavour, a basil flavour, a marjoram flavour, a rosemary flavour, a bayleaf flavour, and a *wasabi* (Japanese horseradish) flavour; a nut flavour such as an almond flavour, a hazelnut flavour, a *Macadamia* nut flavour, a peanut flavour, a pecan flavour, a pistachio flavour, and a walnut flavour; alcoholic flavours, such as a wine flavour, a whisky flavour, a brandy flavour, a rum flavour, a gin flavour, and a liqueur flavour; floral flavours; and vegetable flavours, such as an onion flavour, a garlic flavour, a cabbage flavour, a carrot flavour, a celery flavour, mushroom flavour, and a tomato flavour.

In some embodiments, said flavour co-ingredients include aldehydes and esters such as cinnamyl acetate, cinnamaldehyde, citral diethylacetal, dihydrocarvyl acetate, eugenyl 49 formate, p-methylamisol, and so forth can be used. Further examples of aldehyde flavourings include acetaldehyde (apple), benzaldehyde (cherry, almond), anisic aldehyde (licorice, *anise*), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavours), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), and the like.

Further examples of other flavour co-ingredients can be found in "Chemicals Used in Food Processing", publication 1274, pages 63-258, by the National Academy of Sciences.

Flavour co-ingredients can also include salt tastants, umami tastants, and savoury flavour compounds. Non limiting examples include: NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxylphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide.

In particular embodiments of the present invention, the flavour co-ingredient is selected from the compounds and compositions disclosed in WO2005102701, WO2006009425, WO2005096843, WO2006046853 and WO2005096844, all of which references are herein incorporated by reference in their entirety.

Flavour co-ingredients may include known salt tastants, umami tastants, and savoury flavour compounds. Non limiting examples include: NaCl, KCl, MSG, guanosine monophosphate (GMP), inosin monophospahte (IMP), ribonucleotides such as disodium inosinate, disodium guanylate, N-(2-hydroxyethyl)-lactamide, N-lactoyl-GMP, N-lactoyl tyramine, gamma amino butyric acid, allyl cysteine, 1-(2-hydroxy-4-methoxylphenyl)-3-(pyridine-2-yl)propan-1-one, arginine, potassium chloride, ammonium chloride, succinic acid, N-(2-methoxy-4-methyl benzyl)-N'-(2-(pyridin-2-yl)ethyl) oxalamide, N-(heptan-4-yl)benzo(D)(1,3)dioxole-5-carboxamide, N-(2,4-dimethoxybenzyl)-N'-(2-(pyridin-2-yl)ethyl) oxalamide, N-(2-methoxy-4-methyl benzyl)-N'-2(2-(5-methyl pyridin-2-yl)ethyl) oxalamide, cyclopropyl-E,Z-2,6-nonadienamide.

The carrier material may be employed in flavour compositions according to the invention to encapsulate or to entrap in a matrix the other components of the composition. The role of the carrier material may be merely that of a processing aid or a bulking agent, or it might be employed to shield or protect the other components from the effects of moisture or oxygen or any other aggressive media. The carrier material might also act as a means of controlling the release of flavour from flavour compositions, or edible products.

Carrier materials may include mono, di- or trisaccharides, natural or modified starches, hydrocolloids, cellulose derivatives, polyvinyl acetates, polyvinylalcohols, proteins or pectins. Example of particular carrier materials include sucrose, glucose, lactose, levulose, fructose, maltose, ribose, dextrose, isomalt, sorbitol, mannitol, xylitol, lactitol, maltitol, pentatol, arabinose, pentose, xylose, galactose, maltodextrin, dextrin, chemically modified starch, hydrogenated starch hydrolysate, succinylated or hydrolysed starch, *agar*, carrageenan, gum arabic, gum accacia, tragacanth, alginates, methyl cellulose, carboxymethyl cellulose, hydroxyethyl cellulose, hydroxypropylmethyl cellulose, derivatives and mixtures thereof. Of course, the skilled addresse with appreciate that the cited materials are hereby given by way of example and are not to be interpreted as limiting the invention.

By "adjuvant" is meant an ingredient capable of imparting additional added benefit to flavour compositions or edible products of the present invention such as a colour, light resistance, chemical stability and the like. Suitable adjuvants include solvents (including water, alcohol, ethanol, triacetine, oils, fats, vegetable oil and miglyol), binders, diluents, disintegrating agents, lubricants, colouring agents, preservatives, antioxidants, emulsifiers, stabilisers, anti-caking agents, and the like. In a particular embodiment, the flavour composition comprises an anti-oxidant. Said anti-oxidants may include vitamin C, vitamin E, rosemary extract, antrancine, butylated hydroxyanisole (BHA) and butylated hydroxytoluene (BHT).

Examples of such carriers or adjuvants for flavour compositions or edible products may be found in for example, "Perfume and Flavour Materials of Natural Origin", S. Arctander, Ed., Elizabeth, N. J., 1960; in "Perfume and Flavour Chemicals", S. Arctander, Ed., Vol. I & II, Allured Publishing Corporation, Carol Stream, USA, 1994; in "Flavourings", E. Ziegler and H. Ziegler (ed.), Wiley-VCH Weinheim, 1998, and "CTFA Cosmetic Ingredient Handbook", J. M. Nikitakis (ed.), 1st ed., The Cosmetic, Toiletry and Fragrance Association, Inc., Washington, 1988.

Other suitable and desirable ingredients that may be employed in flavour compositions or edible products are described in standard texts, such as "Handbook of Industrial Chemical Additives", ed. M. and I. Ash, $2^{nd}$ Ed., (Synapse 2000).

Flavour compositions according to the present invention may be provided in any suitable physical form. For example, they may be in the form of oils, emulsions or dispersions in a hydrous liquid or organic liquid suitable for use in edible products, or solid form, such as powders.

Many of the flavour co-ingredients described herein above are volatile and/or may be sensitive to oxidative degradation, particularly when subjected to elevated temperature, and under humid conditions. Accordingly, particular problems can arise when subjecting said co-ingredients described above to dispersive evaporation processes such as spray drying. A non-exhaustive list of ingredients that can be particularly susceptible include, those ingredients containing artificial, natural or synthetic fruit flavours such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. The volatile components of these flavour co-ingredients may include, but are not limited to, acetaldehyde, dimethyl sulfide, ethyl acetate, ethyl propionate, methyl butyrate, and ethyl butyrate. Flavour co-ingredients containing volatile aldehydes or esters include, e.g., cinnamyl acetate, cinnamaldehyde, citral, diethylacetal, dihydrocarvyl acetate, eugenyl formate, and p-methylanisole. Further examples of volatile compounds that may be present as co-ingredients include acetaldehyde (apple); benzaldehyde (cherry, almond); cinnamic aldehyde (cinnamon); citral, i.e., alpha citral (lemon, lime); neral, i.e., beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e., trans-2 (berry fruits); tolyl aldehyde (cherry, almond); veratraldehyde (vanilla); 2,6-dimethyl-5-heptenal, i.e., melonal (melon); 2-6-dimethyloctanal (green fruit); and 2-dodecenal (citrus, mandarin); cherry; or grape and mixtures thereof.

Applicant surprisingly found that the inclusion of a compound of formula (I) in a powder flavour composition, it was possible to obtain flavour quality reminiscent of flavour oils. Accordingly, the invention provides in another of its aspects a method of maintaining flavour quality of a powder flavour composition comprising the step of including in said powder flavour composition a compound of formula (I)

The term edible product as used herein, refers to products for consumption by a subject, typically via the oral cavity (although consumption may occur via non-oral means such as inhalation), for at least one of the purposes of enjoyment, nourishment, or health and wellness benefits. Edible products may be present in any form including, but not limited to, liquids, solids, semi-solids, tablets, capsules, lozenges, strips, powders, gels, gums, pastes, slurries, syrups, aerosols and sprays. The term also refers to, for example, dietary and nutritional supplements. Edible products include products that are placed within the oral cavity for a period of time before being discarded but not swallowed. It may be placed in the mouth before being consumed, or it may be held in the mouth for a period of time before being discarded. An edible product as herein above defined includes products whose taste is modified in the manner described herein by the addition of compounds of formula (I) or whose taste is so modified by processing such that it is enriched in a compound of formula (I).

Broadly, the edible products include, but are not limited to foodstuffs of all kinds, confectionery products, baked products, sweet products, savoury products, fermented products, dairy products, beverages and oral care products.

In a particular embodiment edible products are products for consumption by a subject, typically via the oral cavity (although consumption may occur via non-oral means such as inhalation), for one of the purposes of enjoyment or nourishment.

In a more particular embodiment the edible products are products for consumption by a subject, typically via the oral cavity (although consumption may occur via non-oral means such as inhalation), for the purpose of enjoyment. Still more particularly, they are foodstuffs and beverages.

Exemplary foodstuffs include, but are not limited to, chilled snacks, sweet and savoury snacks, fruit snacks, chips/crisps, extruded snacks, tortilla/corn chips, popcorn, pretzels, nuts, other sweet and savoury snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, uht soup, frozen soup, pasta, canned pasta, dried pasta, chilled/fresh pasta, noodles, plain noodles, instant noodles, cups/bowl instant noodles, pouch instant noodles, chilled noodles, snack noodles, dried food, dessert mixes, sauces, dressings and condiments, herbs and spices, spreads, jams and preserves, honey, chocolate spreads, nut-based spreads, and yeast-based spreads.

Exemplary confectionery products include, but are not limited to, chewing gum (which includes sugarized gum, sugar-free gum, functional gum and bubble gum), center-fill confections, chocolate and other chocolate confectionery, medicated confectionery, lozenges, tablets, pastilles, mints, standard mints, power mints, chewy candies, hard candies, boiled candies, breath and other oral care films or strips, candy canes, lollipops, gummies, jellies, fudge, caramel, hard and soft panned goods, toffee, taffy, licorice, gelatin candies, gum drops, jelly beans, nougats, fondants, combinations of one or more of the above, and edible flavour compositions incorporating one or more of the above.

Exemplary baked products include, but are not limited to, alfajores, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savoury biscuits and crackers, bread substitutes, Exemplary sweet products include, but are not limited to, breakfast cereals, ready-to-eat ("rte") cereals, family breakfast cereals, flakes, muesli, other ready to eat cereals, children's breakfast cereals, hot cereals, Exemplary savoury products include, but are not limited to, salty snacks (potato chips, crisps, nuts, tortilla-tostada, pretzels, cheese snacks, corn snacks, potato-snacks, ready-to-eat popcorn, microwaveable popcorn, pork rinds, nuts, crackers, cracker snacks, breakfast cereals, meats, aspic, cured meats (ham, bacon), luncheon/breakfast meats (hotdogs, cold cuts, sausage), tomato products, margarine, peanut butter, soup (clear, canned, cream, instant, UHT), canned vegetables, pasta sauces.

Exemplary dairy products include, but are not limited to, cheese, cheese sauces, cheese-based products, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavoured, functional and other condensed milk, flavoured milk drinks, dairy only flavoured milk drinks, flavoured milk drinks with fruit juice, soy milk, sour milk drinks, fermented dairy drinks, coffee whiteners, powder milk, flavoured powder milk drinks, cream, yoghurt, plain/natural yoghurt, flavoured yoghurt, fruited yoghurt, probiotic yoghurt, drinking yoghurt, regular drinking yoghurt, probiotic drinking yoghurt, chilled and shelf-stable desserts, dairy-based desserts, soy-based desserts.

Exemplary beverages include, but are not limited to, flavoured water, soft drinks, fruit drinks, coffee-based drinks, tea-based drinks, juice-based drinks (includes fruit and vegetable), milk-based drinks, gel drinks, carbonated or non-carbonated drinks, powdered drinks, alcoholic or non-alcoholic drinks.

Exemplary fermented foods include, but are not limited to, Cheese and cheese products, meat and meat products, soy and soy products, fish and fish products, grain and grain products, fruit and fruit products.

In a particular embodiment the consumable product is selected from the group consisting of soy sauce, cheese, soup, hot and cold sauces, fruits, vegetables, ketchups, tea, coffee, snacks such as potato chips or extruded snacks.

The compounds of formula (I), when added to a flavour composition and/or an edible product act to complement the flavour and/or mouthfeel to render it more delicious and authentic. The effects may be temporal or related to intensity, for example the compounds may act by enhancing, strengthening, softening, sharpening a flavour, or making more salivating. The compounds of formula (I) may also affect the temporal profile of a flavour, that is, they may affect the initial impact of a flavour, the body of a flavour, or its lingering effect.

The compounds of formula (I) may modify any aspect of the temporal profile of taste or flavour of a flavour composition or edible product. In particular, the compounds improve mouth feel and impart more creamy and fatty sensations.

Compounds of formula (I) or flavour compositions containing same may be added to edible products in widely carrying amounts. The amount will depend on the nature of the edible product to be flavoured, and on the desired effect, as well as on the nature of the ingredients present in said flavour composition.

Preferably however, the beneficial effects attributed to the presence of a compound of formula (I) can be achieved if the compound (or compounds, if a mixture of compounds is to be employed), employed alone or in a flavour composition, is dosed in such amounts that the compound(s) is/are present in amounts of 1 part per billion to 10 parts per million based on the total weight of the edible product. Whereas amounts higher than this can be employed, the beneficial effects are considerably less apparent and undesirable off-notes can become increasingly apparent.

Interesting organoleptic effects, e.g. salt, alcohol or coolant boosting effects, in edible products containing salt or alcohol or coolant compounds can be achieved when compound(s) of the formula (I) is/are employed at levels of 1 to 100 ppb.

Interesting organoleptic effects, for example umami boosting effects, in edible products containing umami tastants can be achieved when compound(s) of the formula (I) is/are employed at levels of 100 to 250 ppb.

Interesting organoleptic effects, in particular mouthfeel boosting effects, in edible products can be achieved when compound(s) of the formula (I) is/are employed at levels of 250 to 500 ppb.

Interesting organoleptic effects, e.g. fat boosting effects, in edible products containing fats can be achieved when compound(s) of the formula (I) is/are employed at levels of 500 to 1000 ppb.

It is particularly advantageous to incorporate compounds of formula (I) into edible products that are formed under conditions of high temperature, such as baking, frying or which are processed by heat treatments such as pasteurization or under UHT conditions. Under high preparation or processing temperatures, volatile flavour ingredients may be lost or degraded with the result that flavour intensity can be reduced and the essential and authentic flavour characteristics can be diminished. Such edible products include dairy products, snack foods, baked products, powdered soft drinks and similar dry mixes, and the like, fats and condiments, mayonnaise, dressings, soups and bouillons, and beverages.

Particularly preferred classes of edible product according to the present invention are powdered soft drinks and similar dry mix applications. Dry mix applications are known in the art and included products in powder form that are intended to be reconstituted before consumption. They include powdered soups, powdered cake mixes, powdered chocolate drinks, instant coffees, seasonings and fonds, and the like.

Dry powders formed by dispersive evaporation processes, such as spray drying, represent a very convenient vehicle to deliver flavour oil quality flavours to edible products.

Unfortunately, flavour oils, and in particular citrus flavour oils can be particularly sensitive to dispersive evaporation processes, especially processes carried out at high temperature. Flavour oils tend to evaporate or degrade to form products having unfavourable off-notes. Powdered flavour compositions, particularly those containing citrus oils, can be of poor quality and exhibit relatively short self-life, as a result.

Surprisingly, the incorporation of compounds of formula (I) or flavour compositions containing same into powder products, results in powder products that exhibit the impact and authenticity of the flavour oils used in their preparation, essentially maintaining flavour oil quality in a powdered flavour formulations.

Accordingly, the invention provides in another aspect a powder flavour product comprising a compound according to formula (I) and at least one additional flavour co-ingredient.

In another aspect of the invention there is provided a powder soft drink product or other dry mix product comprising a compound according to formula (I).

In yet another aspect of the present invention there is provided a powdered soft drink product or other dry mix product comprising a powder flavour composition comprising a compound of formula (I).

In yet another aspect of the present invention there is provided a method of forming a powder flavour product comprising the step of incorporating into said composition a compound according to formula (I).

In a particular embodiment of the compound of formula (I) may be added to the formed powder flavour product, or it may be added to flavour composition before forming the powder product.

Another particularly preferred class of edible product according to the present invention is snack food. Snack food is a category of product well known to the skilled person in the food industry. These products are described above and include, without limitation, pretzels, corn chips, potato chips, puffed products, extruded products, tortilla chips and the like. Still more particularly, the invention is concerned with low fat snack food compositions. Low fat snack food compositions contain less that 30% by weight fat, more particularly between 5 to 25% by weight of fat.

A problem with reducing fat in a snack food product is the loss in taste and texture. Fats play an important role in the way that dough behaves during processing and greatly affect the quality, flavor and texture of ready-to-eat products. As the fat content in snack products is reduced or replaced with other ingredients (e.g., non-digestible fat, protein, fiber, gums), adverse organoleptic effects (e.g., mouth coating, drying, lack of crispness and lack of flavour) are increased. The adverse organoleptic effects result in products having reduced palatability.

Considerable efforts have been expended in devising flavour compositions to overcome the problems associated with low fat snack food products. Flavours may be applied to a snack food as topical coatings in the form of dry powders and/or as liquids (e.g., oil-based, water-based). Another approach has been to add flavour to the dough.

Despite these various approaches which have been taken to improve consumer appeal and palatability of snack foods, and particularly low fat snack foods, there is still a need for improved low-fat snack foods having coatings applied thereto with the visual appeal, flavour, and texture of full-fat snack foods.

Compounds according to formula (I) or flavour compositions containing same can be incorporated into snack foods to impart an impactful flavour and a mouth feel with a remarkable roundness and fullness. Furthermore, the taste and mouth feel effects can be achieved even in low fat snack foods.

Accordingly, the invention provides in another of its aspects a snack food comprising a flavour composition as hereinabove described. In a particular embodiment of the invention the snack food has a fat content of about 40% or less by weight based on the total weight of the snack food, more particularly about 30% or less, still more particularly 25% or less, more particularly still about 10% or less, still more particularly about 5% or less, still more particularly about 3% or less.

Examples of snack foods are described above and include products processed by oven baking, extrusion or frying, and which are made from potato and/or corn and/or various grains such as rice or wheat.

Another particularly preferred class of edible product according to the present invention is alcoholic beverages.

Applicant surprisingly found that compounds according to formula (I) incorporated into an alcoholic beverage had the effect of increasing the alcohol impact of the beverage.

Accordingly, the invention provides in another of its aspects an alcoholic beverage comprising a compound according to formula (I).

In yet another aspect of the invention there is provided a method of producing a heightened alcoholic impression in an alcoholic beverage by incorporating into said beverage a compound according to formula (I).

Compounds of formula (I) may be incorporated into said alcoholic beverage in amounts of 1 ppb to 1 ppm.

Other classes of edible product are products taken orally in the form of tablets, capsules, powders, multiparticulates and the like. Such products may include pharmaceutical dosage forms or nutraceutical dosage forms.

Certain groups of people have problems swallowing tablets or capsules, powders, multi-particulates and the like. This problem can be particularly pronounced in certain consumer groups, such as children and the very old or infirm. Applicant surprisingly found that compounds according to the formula (I) when taken into the oral cavity produce a pronounced salivating effect. Incorporating the compounds into these forms, particularly as part of a coating around said dosage forms can ease the swallowing process for consumers, in particular children and the old or infirm.

Accordingly, the invention provides in another of its aspects an orally administrable dosage form, in particular in the form of tablets capsules, powders or multi-particulates comprising a compound according to the formula (I).

Another preferred class of edible product is baked goods. Compounds of the formula (I) may be incorporated topically or in-dough. Incorporated at levels of 1 ppb to 1 ppm, the compounds of formula (I) render baked products less dry and more succulent.

Other preferred class of edible products are caloric or non-caloric beverages containing carbohydrate sweeteners, such as sucrose, high fructose corn syrup, fructose and glucose, or high intensity, non-nutritive sweeteners such as aspartame, acesulfame K, sucralose, cyclamate, sodium saccharin, neotame, rebaudioside A, and/or other *Stevia*-based sweeteners; as well as other optional ingredients such as juices, organic acids such as citric acid, alcohol and functional ingredients.

Incorporated at levels of 1 ppb to 10 ppm, compounds of formula (I) impart to said beverages containing sweeteners at levels of less than 1% and up to about 20%, an up-front sweetness and mouthfeel that is reminiscent of sugar.

Other preferred edible products are savoury products, in particular those that are soy-based or fish-based.

Incorporated at levels of 1 ppb to 10 ppm, in a soy-based products (such as soy sauce) or a fish-based product (such as fish sauce) containing 5 to 40% salt, the products are found to exhibit strong umami tastes that are long-lasting and rich.

Another preferred edible product is a clouded beverage product.

Certain beverages such as juices have relatively higher turbidity and thus have an opaque appearance. Often, it is desired that the beverage have a relatively high turbidity. This might be desirable to provide a more natural appearance to beverages with low juice content, or it might be for reasons related to masking sedimentation or "ringing" (where flavour or colour oils rise to the surface of a container during storage). Clouded beverages are usually formed by means of a clouding agent. Clouding agents are usually supplied in the form of emulsions, or the clouding agent may be part of a powdered beverage that upon reconstitution will formed an emulsion providing a permanent cloud to the beverage.

Compounds of the formula (I), in addition to their organoleptic properties, can lend stability to clouding agents and to beverage compositions containing same.

Accordingly, the invention provides in another of its aspects a composition comprising a beverage clouding composition and a compound of formula (I).

In a particular embodiment of the invention, a flavour composition as herein defined may be provided in the form of an emulsion. This emulsion composition may be particularly useful in clouded beverage applications, in particular, in which it is intended to employ a clouding agent.

In yet another aspect of the invention there is provided a clouded beverage composition comprising a clouding agent and a compound of the formula (I).

Other preferred edible products are those that are formed by a process of ripening.

In food processing, it frequently occurs that a food needs to remain for a prolonged period of time and under well-defined conditions to obtain the food with the requisite and recognised quality. A commonly used term for this process is ripening. Ripening is well known in the processing of certain types of cheese, meat, soy-sauce and wine, as well as beer sausage, sauerkraut, tempeh and tofu. There are also specific steps that are carried out for specific reasons (such as water-removal, or off-note removal) that have beneficial effects on the food products. Examples of this are the conching of chocolate and the drying of noodles, vegetables and fruits. The transformations that improve the quality of the food are induced by chemical conversions, enzymatically catalysed conversions or fermentative transformations. All of these conversions are slow and therefore expensive; they are also not fully predictable or controllable.

The compounds of formula (I), having regard to the property of adding to the authentic taste characteristics of the edible products in which they are incorporated, may be added to an edible product during its ripening process in order to reduce storage time without adversely influencing the taste quality of the ripened product.

Accordingly, in another aspect of the invention there is provided a method of ripening a product selected from the group consisting of cheese, meat, soy-sauce and wine, beer, sausage, sauerkraut, tempeh and tofu, comprising the step of ripening the product in the presence of a compound according to the formula (I).

In another aspect of the invention there is provided a method of conching chocolate, said method comprising the step of adding to the chocolate a compound according to the formula (I), or a flavour composition containing same.

There now follows a series of non-limiting examples that serve to illustrate the invention.

EXAMPLE 1

Preparation

Linoleoyl Chloride 1026 grams (3.659 moles (assuming 100% purity), 1.0 equiv.) of linoleic acid (mixture of fatty acids, approximately 60% pure based on linoleic acid moiety) and 8210 grams of THF (0.13% water) were mixed together in a reaction vessel. While stirring and cooling (cooling water temperature 18.6° C.) 948 grams (7.32 moles, 2.0 equivalents) of oxalyl dichloride 98% (Sigma Aldrich) was dosed in 50 minutes. Thereafter, stirring was continued for 120 minutes at room temperature (22° C.).

The reaction crude was concentrated in two steps. First distillation at 180 mbar\40° C. was carried out to obtain 5594 grams of distillate. This was removed and transferred to a rotary evaporator. Concentrating was continued till 55° C. and 30 mbar (reached in steps). The distillate (518 grams) was added to the earlier obtained solvent and excess oxalyl dichloride. The clear dark brown concentrate (1170 grams) will be used in the next step.

Preparation 4-((9Z,12Z)-octadeca-9,12-dienamido)butanoic Acid (C18:2-GABA or GABA Linoleic Acid Compound) Solution in Propylene Glycol A reaction vessel was charged with a mixture of 7016 grams of water and 280.7 grams (7.02 moles) of sodium hydroxide pellets. To the mixture was added 401.5 grams (3.89 moles, 1.247 equiv.) of gamma amino butyric acid (GABA) and 6244.6 grams of THF. While stirring the contents were cooled to 10° C. Over a period of 1 hour, 935.5 grams (3.13 moles (based on 100% purity, 1.0 equiv.) of linoleoyl chloride prepared in accordance with the aforementioned method added to the mixture. During the dosage the temperature range was 10° C.-6.5° C. While cooling stirring was continued for 1 hour, the temperature was 6.5° C. Cooling was stopped and stirring was continued for an additional hour, the temperature rose to 8.0° C.

The crude product was acidified by dosing 579 grams (5.79 moles) of hydrochloric acid 36%. The pH was adapted from 12.17 to 2.0. After the addition of the acid, stirring was stopped and the mixture was allowed to separate.

After the separation the light yellow lower aqueous phase was removed. The brown organic top phase was stored. The lower aqueous phase was extracted with 3898 grams of ethyl acetate. After stirring and separating the lower phase (8881 grams) was removed and stored. The ethyl acetate top phase (6375 grams) was added to the earlier obtained organic phase.

The combined mixture was washed with a brine solution made out of 585 grams of sodium chloride and 5262 grams of water. After stirring and separating, the lower brine phase (6800 grams) was removed and the brown organic top phase was concentrated in two steps. Step 1 was concentrated at 40° C. and 170 mbar, whereas in step 2a rotary evaporator was employed to remove more solvent (and water) at 55° C. and 32 mbar. In total (steps 1 and 2) 6860 grams of distillate were obtained. 1,2-propylene glycol (PG) was added.

To the product\PG mixture 3235 grams of heptane and 312 grams of water was added. The entire mixture was added to a 10 liter separatory funnel. After shaking and separating, two phases were visible. The lower PG\product phase (4385 grams) was removed and the top heptane phase (2115 grams) was stored.

Residual solvents in the product/propylene glycol (PG) phase were removed in a rotaty evaporator at 55° C. and 22 mbar (reached in steps). As the solvents and water were removed the PG\product mixture became clear. In the end 762 grams of distillate were obtained.

EXAMPLE 2

A spray dried powder of the GABA-Linoleic compound produced in Example 1 was prepared in the following manner:

400 grams of maltodextrin (DE12) was added to 600 grams of water and 26.7 grams of a propylene glycol solution (representing 1% of the GABA-linoleic acid compound after drying) to form a mixture. The mixture was stirred vigorously at 20 degrees centigrade in an equal volume of water to form a feed. The feed is homogenized using an Ultra Turrax T25 at 25,000 rpm for about 2 minutes. The homogenised feed is spray-dried in a NIRO MOBIL MINOR SPRAY DRYER using a rotary wheel atomiser at 20,000 rpm. Inlet air temperature is kept at 190° C., resulting in an outlet temperature in the range of 90° C.

A dried powder containing 1% GABA-linoleic acid compound was obtained.

The powder was equilibrated in a dessicator above a saturated salt solution for 2 weeks under conditions of 50% relative humidity. Thereafter, the Tg of the equilibrated powder was measured by DSC (Perkin Elmer Pyrus Diamond DSC) using a closed cup method, as follows: A stainless steel cup is filled with the equilibrated powder and closed such that no water can evaporate during measurement. DSC measurement is undertaken using the heat-cool-heat measurement wherein heating is carried out at 10° C./min; cooling at 40° C./min; and heating again at 10° C./min. The Tg measurement is calculate from the mid-point of a curve produced when heat flow is plotted against temperature on the second heat cycle.

The invention claimed is:

1. A method of isolating and recovering a compound according to the formula (I) which exhibits taste modifying properties when incorporated within an edible composition or within a flavour composition,

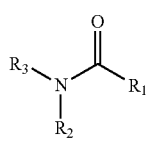

(I)

wherein
$R_1$ together with the carbonyl group to which it is attached is a residue of a
carboxylic acid, and
$NR_2R_3$, in which $R_3$ is H or together with $R_2$ and the N-atom to which they are attached, a 5-membered ring, is a residue of an amino acid;
from a reaction mixture comprising the compound in a reaction solvent, the method comprising the steps of:
prior to removal of reaction solvent from the reaction mixture by evaporation, adding to the reaction mixture an extraction solvent for the compound, said extraction solvent having a higher boiling point than the reaction solvent, and
subsequent to the evaporation of and removal of the reaction solvent from the reaction mixture containing the compound of formula (I), the reaction solvent and the extraction solvent, the compound of formula (I) is recovered in the form of a stock solution containing the compound of formula (I) in the extraction solvent.

2. A method of forming a stock solution comprising the steps of:
isolating and recovering a compound which exhibits taste modifying properties when incorporated within an edible composition or within a flavour composition according to the formula (I)

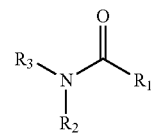

(I)

wherein
$R_1$ together with the carbonyl group to which it is attached is a residue of a
carboxylic acid, and
$NR_2R_3$, in which $R_3$ is H or together with $R_2$ and the N-atom to which they are attached, a 5-membered ring, is a residue of an amino acid;
from a reaction mixture comprising the compound in a reaction solvent, the method comprising the steps of:
prior to removal of the reaction solvent from the reaction mixture by evaporation, adding to the reaction mixture an extraction solvent for the compound which has a higher boiling point than the boiling point of the reaction solvent, and,
subsequently, separating the compound according to formula (I) from the reaction solvent, and recovering from the reaction mixture a stock solution containing the compound and the extraction solvent.

3. A method according to claim 1 wherein the extraction solvent is selected from water-miscible alcohols and derivatives thereof.

4. A method according to claim 3 wherein the extraction solvent is selected from: ethanol, glycerol, propylene glycol, triacetine or miglyol, or mixtures thereof.

5. A method according to claim 3, wherein the extraction solvent is propylene glycol.

6. A stock solution comprising up to 25% by weight of a compound of formula (I) which exhibits taste modifying properties when incorporated within an edible composition or within a flavour composition

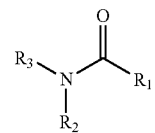

(I)

wherein
$R_1$ together with the carbonyl group to which it is attached is a residue of a
carboxylic acid, and $NR_2R_3$, in which $R_3$ is H or together with $R_2$ and the N-atom to which they are attached, a 5-membered ring, is a residue of an amino acid;
in a solvent selected from water-miscible alcohols and/or derivatives thereof.

7. A stock solution according to claim 6 wherein the solvent is selected from: ethanol, glycerol, ethylene glycol, propylene glycol, triacetine or miglyol, or mixtures thereof.

8. A stock solution according to claim 6, wherein the solvent is propylene glycol.

9. A stock solution according to claim 6 wherein the compound of formula (I) is present in an amount of up to 15% by weight.

10. A spray dried powder comprising a compound according to formula (I) which exhibits taste modifying properties when incorporated within an edible composition or within a flavour composition

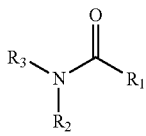
(I)

wherein
R₁ together with the carbonyl group to which it is attached is a residue of a
carboxylic acid, and NR₂R₃, in which R₃ is H or together with R₂ and the N-atom to which they are attached, a 5-membered ring, is a residue of an amino acid.

11. A spray dried powder according to claim 10, comprising a carrier material selected from a maltodextrin having a dextrose equivalent (DE) of 3 to 25, or gum Arabic.

12. A spray dried powder according to claim 10 wherein the compound of formula (I) is present in an amount of up to 1.5% by weight based on the total weight of the powder.

13. A spray dried powder according to claim 10 formed from a stock solution comprising up to 25% by weight of a compound of formula (I)

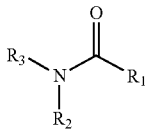
(I)

wherein
R₁ together with the carbonyl group to which it is attached is a residue of a
carboxylic acid, and NR₂R₃, in which R₃ is H or together with R₂ and the N-atom to which they are attached, a 5-membered ring, is a residue of an amino acid.

14. The method according to claim 1, wherein:
the residue of an amino acid is selected from: a proteinogenic amino acid, ornithine, gamma-aminobutyric acid or beta alanine, or a 1-amino cycloalkyl carboxylic acid.

15. The method according to claim 2, wherein:
the residue of an amino acid is selected from: a proteinogenic amino acid, ornithine, gamma-aminobutyric acid or beta alanine, or a 1-amino cycloalkyl carboxylic acid.

16. The stock solution according to claim 6, wherein:
the residue of an amino acid is selected from: a proteinogenic amino acid, ornithine, gamma-aminobutyric acid or beta alanine, or a 1-amino cycloalkyl carboxylic acid.

17. The method according to claim 1, wherein the stock solution contains 5% to 30% by weight of the compound of formula (I).

18. The method according to claim 2, wherein the stock solution contains 5% to 30% by weight of the compound of formula (I).

19. The method according to claim 1, wherein the compound of formula (I) is represented by the following structure:

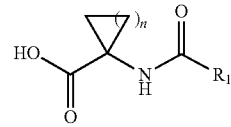

and wherein:

n is 1, 2, 3 or 4.

20. The method according to claim 1, wherein the compound of formula (I) is represented by the following structure:

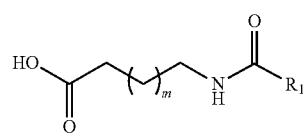

and wherein:

m is 0 or 1.

21. The method according to claim 1, wherein the compound of formula (I) is represented by the following structure:

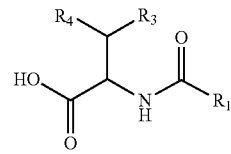

and wherein:

R₃ is hydrogen is methyl, and

R₄ is methyl, ethyl or iso-propyl.

22. The method according to claim 1, wherein the compound of formula (I) is represented by the following structure:

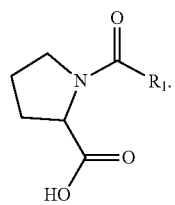

23. The method according to claim 1, wherein the compound of formula (I) is represented by the following structure:

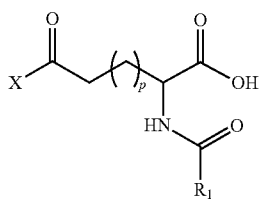

and wherein:
X is OH or is NH$_2$, and
P is 0 or 1.

24. The method according to claim 1, wherein the compound of formula (I) is represented by the following structure:

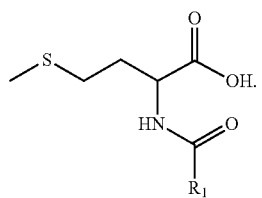

25. The method according to claim 1, wherein the compound of formula (I) is represented by the following structure:

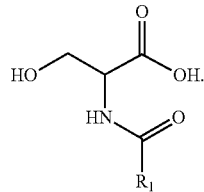

26. The stock solution according to claim 6, which is a flavour composition which in addition to the compound of formula (I) additionally comprises at least one flavour co-ingredient.

27. The spray dried powder of claim 10, wherein NR$_2$R$_3$ is a proteinogenic amino acid, ornithine, gamma-aminobutyric acid or beta alanine, or a 1-amino cycloalkyl carboxylic acid.

28. The stock solution of claim 26, which further comprises a carrier material, or at least one adjuvant.

* * * * *